United States Patent
Janssens et al.

(10) Patent No.: US 7,544,694 B2
(45) Date of Patent: Jun. 9, 2009

(54) SUBSTITUTED DIAZA-SPIRO-[5.5]-UNDECANE DERIVATIVES AND THEIR USE AS NEUROKININ ANTAGONISTS

(75) Inventors: Frans Eduard Janssens, Bonheide (BE); Bruno Schoentjes, Bois-Guillaume (FR); Sophie Coupa, Louviers (FR); Alain Philippe Poncelet, Le Manoir sur Seine (FR); Yvan René Ferdinand Simonnet, Rouen (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/547,889

(22) PCT Filed: Apr. 4, 2005

(86) PCT No.: PCT/EP2005/051508

§ 371 (c)(1),
(2), (4) Date: Oct. 5, 2006

(87) PCT Pub. No.: WO2005/097795

PCT Pub. Date: Oct. 20, 2005

(65) Prior Publication Data

US 2007/0232636 A1 Oct. 4, 2007

(30) Foreign Application Priority Data

Apr. 6, 2004 (WO) ................ PCT/EP2004/050457

(51) Int. Cl.
*A61K 31/438* (2006.01)
*C07D 471/10* (2006.01)
(52) U.S. Cl. .................. 514/278; 546/16; 544/238; 544/336; 544/349; 514/249; 514/252
(58) Field of Classification Search .............. 514/278, 514/249, 252; 546/16; 544/238, 336, 349
See application file for complete search history.

(56) References Cited

U.S. PATENT DOCUMENTS 6,169,097 B1 * 1/2001 Janssens et al. ............. 514/316

* cited by examiner

*Primary Examiner*—Charanjit S Aulakh
(74) *Attorney, Agent, or Firm*—Woodcock Washburn LLP

(57) ABSTRACT

This invention concerns substituted diaza-spiro-[5.5]-undecane derivatives having neurokinin antagonistic activity, in particular $NK_1$ antagonistic activity, a combined $NK_1/NK_2$ antagonistic activity, a combined $NK_1/NK_3$ antagonistic activity and a combined $NK_1/NK_2/NK_3$ antagonistic activity, their preparation, compositions comprising them and their use as a medicine, in particular for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, COPD and micturition disorders such as urinary incontinence.

The compounds according to the invention can be represented by general Formula (I)

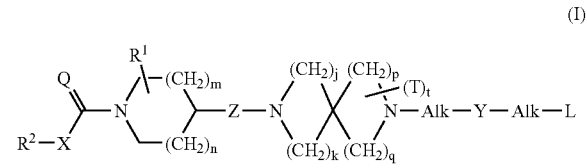

(I)

and comprises also the pharmaceutically acceptable acid or base addition salts thereof, the stereochemically isomeric forms thereof, the N-oxide form thereof and prodrugs thereof, wherein all substituents are defined as in Claim 1.

14 Claims, No Drawings

SUBSTITUTED DIAZA-SPIRO-[5.5]-UNDECANE DERIVATIVES AND THEIR USE AS NEUROKININ ANTAGONISTS

CROSS REFERENCE TO RELATED APPLICATIONS

This application is the national stage of Application No. PCT/EP2005/051508, filed 4 Apr. 2005. which application claims priority from PCT/EP2004/050457 filed 6 Apr. 2004.

FIELD OF THE INVENTION

This invention concerns substituted diaza-spiro-[5.5]-undecane derivatives having neurokinin antagonistic activity, in particular $NK_1$ antagonistic activity, a combined $NK_1/NK_2$ antagonistic activity, a combined $NK_1/NK_3$ antagonistic activity and a combined $NK_1/NK_2/NK_3$ antagonistic activity, their preparation, compositions comprising them and their use as a medicine, in particular for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence.

BACKGROUND OF THE INVENTION

Tachykinins belong to a family of short peptides that are widely distributed in the mammalian central and peripheral nervous system (Bertrand and Geppetti, *Trends Pharmacol. Sci.* 17:255-259 (1996); Lundberg, *Can. J. Physiol. Pharmacol.* 73:908-914 (1995); Maggi, *Gen. Pharmacol.* 26:911-944 (1995); Regoli et al., *Pharmacol. Rev.* 46 (1994)). They share the common C-terminal sequence Phe-Xaa-Gly-Leu-Met-$NH_2$. Tachykinins released from peripheral sensory nerve endings are believed to be involved in neurogenic inflammation. In the spinal cord/central nervous system, tachykinins may play a role in pain transmission/perception and in some autonomic reflexes and behaviors. The three major tachykinins are Substance P (SP), Neurokinin A (NKA) and Neurokinin B (NKB) with preferential affinity for three distinct neurokinin receptor subtypes, termed $NK_1$, $NK_2$, and $NK_3$, respectively. However, functional studies on cloned receptors suggest strong functional cross-interaction between the 3 tachykinins and their corresponding neurokinin receptors (Maggi and Schwartz, *Trends Pharmacol. Sci.* 18: 351-355 (1997)).

Species differences in structure of $NK_1$ receptors are responsible for species-related potency differences of $NK_1$ antagonists (Maggi, *Gen. Pharmacol.* 26:911-944 (1995); Regoli et al., *Pharmacol. Rev.* 46(4):551-599 (1994)). The human $NK_1$ receptor closely resembles the $NK_1$ receptor of guinea-pigs and gerbils but differs markedly from the $NK_1$ receptor of rodents. The development of neurokinin antagonists has led to date to a series of peptide compounds of which might be anticipated that they are metabolically too labile to be employed as pharmaceutically active substances (Longmore J. et al., *DN&P* 8(1):5-23 (1995)).

The tachykinins are involved in schizophrenia, depression, (stress-related) anxiety states, emesis, inflammatory responses, smooth muscle contraction and pain perception. Neurokinin antagonists are in development for indications such as emesis, anxiety and depression, irritable bowel syndrome (IBS), circadian rhythm disturbances, visceral pain, neurogenic inflammation, asthma, micturition disorders, and nociception. In particular, $NK_1$ antagonists have a high therapeutic potential in emesis and depression and $NK_2$ antagonists have a high therapeutic potential in asthma treatments. $NK_3$ antagonists seem to play a role in the treatment of pain/inflammation (Giardina, G. et al. *Exp. Opin. Ther. Patents*, 10(6): 939-960 (2000)) and schizophrenia.

Schizophrenia

The NK3 antagonist SR142801 (Sanofi) was recently shown to have antipsychotic activity in schizophrenic patients without affecting negative symptoms (Arvantis, L. *ACNP Meeting,* December 2001). Activation of $NK_1$ receptors causes anxiety, stressful events evoke elevated substance P (SP) plasma levels and $NK_1$ antagonists are reported to be anxiolytic in several animal models. The $NK_1$ antagonist from Merck, MK-869 shows antidepressant effects in major depression, but data were not conclusive due to a high placebo response rate. Moreover, the $NK_1$ antagonist from Glaxo-Welcome (S)-GR205,171 was shown to enhance dopamine release in the frontal cortex but not in the striatum (Lejeune et al. *Soc. Neurosci.,* November 2001). It is therefore hypothesized that $NK_3$ antagonism in combination with $NK_1$ antagonism would be beneficial against both positive and negative symptoms of schizophrenia.

Anxiety and Depression

Depression is one of the most common affective disorders of modern society with a high and still increasing prevalence, particularly in the younger members of the population. The life time prevalence rates of Major depression (MDD, DSM-IV) is currently estimated to be 10-25% for women and 5-12% for men, whereby in about 25% of patients the life time MDD is recurrent, without full inter-episode recovery and superimposed on dysthymic disorder. There is a high co-morbidity of depression with other mental disorders and, particularly in younger population high association with drug and alcohol abuse. In the view of the fact that depression primarily affects the population between 18-44 years of age e.g. the most productive population, it is obvious that it imposes a high burden on individuals, families and the whole society.

Among all therapeutic possibilities, the therapy with antidepressants is incontestably the most effective. A large number of antidepressants have been developed and introduced to the market in the course of the last 40 years. Nevertheless, none of the current antidepressants fulfill all criteria of an ideal drug (high therapeutic and prophylactic efficacy, rapid onset of action, completely satisfactory short- and long-term safety, simple and favourable pharmacokinetics) or is without side effects which in one or the other way limits their use in all groups and subgroups of depressed patients.

Since no treatment of the cause of depression exists at present, nor appears imminent, and no antidepressant is effective in more than 60-70% of patients; the development of a new antidepressant which may circumvent any of the disadvantages of the available drugs is justified.

Several findings indicate involvement of SP in stress-related anxiety states. Central injection of SP induces a cardiovascular response resembling the classical "fight or flight" reaction characterised physiologically by vascular dilatation in skeletal muscles and decrease of mesenteric and renal blood flow. This cardiovascular reaction is accompanied by a behavioral response observed in rodents after noxious stimuli or stress (Culman and Unger, *Can. J Physiol. Pharmacol.* 73:885-891 (1995)). In mice, centrally administered $NK_1$ agonists and antagonists are anxiogenic and anxiolytic, respectively (Teixeira et al., *Eur. J. Pharmacol.* 311:7-14 (1996)). The ability of $NK_1$ antagonists to inhibit thumping induced by SP (or by electric shock; Ballard et al., *Trends Pharmacol. Sci.* 17:255-259 (2001)) might correspond to this antidepressant/anxiolytic activity, since in gerbils thumping plays a role as an alerting or warning signal to conspecifics.

The $NK_1$ receptor is widely distributed throughout the limbic system and fear-processing pathways of the brain, including the amygdala, hippocampus, septum, hypothalamus, and periaqueductal grey. Additionally, substance P is released centrally in response to traumatic or noxious stimuli and substance P-associated neuro-transmission may contribute to or be involved in anxiety, fear, and the emotional disturbances that accompany affective disorders such as depression and anxiety. In support of this view, changes in substance P content in discrete brain regions can be observed in response to stressful stimuli (Brodin et al., *Neuropeptides* 26:253-260 (1994)).

Central injection of substance P mimetics (agonists) induces a range of defensive behavioral and cardiovascular alterations including conditioned place aversion (Elliott, *Exp. Brain. Res.* 73:354-356 (1988)), potentiated acoustic startle response (Krase et al., *Behav. Brain. Res.* 63:81-88 (1994)), distress vocalisations, escape behaviour (Kramer et al., *Science* 281:1640-1645 (1998)) and anxiety on the elevated plus maze (Aguiar and Brandao, *Physiol. Behav.* 60:1183-1186 (1996)). These compounds did not modify motor performance and co-ordination on the rotarod apparatus or ambulation in an activity cage. Down-regulation of substance P biosynthesis occurs in response to the administration of known anxiolytic and antidepressant drugs (Brodin et al., *Neuropeptides* 26:253-260 (1994); Shirayama et al., *Brain. Res.* 739:70-78 (1996)). Similarly, a centrally administered $NK_1$ agonist-induced vocalisation response in guinea-pigs can be antagonized by antidepressants such as imipramine and fluoxetine as well as L-733,060, an $NK_1$ antagonist. These studies provide evidence suggesting that blockade of central $NK_1$ receptors may inhibit psychological stress in a manner resembling antidepressants and anxiolytics (Rupniak and Kramer, *Trends Pharmacol. Sci.* 20:1-12 (1999)), but without the side effects of present medications.

Emesis

Nausea and vomiting are among the most distressing side effects of cancer chemotherapy. These reduce the quality of life and may cause patients to delay or refuse, potentially curative drugs (Kris et al., *J. Clin. Oncol.*, 3:1379-1384 (1985)). The incidence, intensity and pattern of emesis is determined by different factors, such as the chemotherapeutic agent, dosage and route of administration. Typically, early or acute emesis starts within the first 4 h after chemotherapy administration, reaching a peak between 4 h and 10 h, and decreases by 12 to 24 h. Delayed emesis (developing after 24 h and continuing until 3-5 days post chemotherapy) is observed with most 'high-emetogenic' chemotherapeutic drugs (level 4 and 5 according to Hesketh et al., *J. Clin. Oncol.* 15:103 (1997)). In humans, these 'high-emetogenic' anti-cancer treatments, including cis-platinum, induce acute emesis in >98% and delayed emesis in 60-90% of cancer patients.

Animal models of chemotherapy such as cisplatin-induced emesis in ferrets (Rudd and Naylor, *Neuropharmacology* 33:1607-1608 (1994); Naylor and Rudd, *Cancer. Surv.* 21:117-135 (1996)) have successfully predicted the clinical efficacy of the 5-$HT_3$ receptor antagonists. Although this discovery led to a successful therapy for the treatment of chemotherapy- and radiation-induced sickness in cancer patients, 5-$HT_3$ antagonists such as ondansetron and granisetron (either or not associated with dexamethasone) are effective in the control of the acute emetic phase (the first 24 h) but can only reduce the development of delayed emesis (>24 h) with poor efficacy (De Mulder et al., *Annuals of Internal Medicine* 113:834-840 (1990); Roila, *Oncology* 50:163-167 (1993)). Despite these currently most effective treatments for the prevention of both acute and delayed emesis, still 50% of patients suffer from delayed vomiting and/or nausea (Antiemetic Subcommittee, *Annals Oncol.* 9:811-819 (1998)).

In contrast to 5-$HT_3$ antagonists, $NK_1$ antagonists such as CP-99,994 (Piedimonte et al., *L. Pharmacol. Exp. Ther.* 266: 270-273 (1993)) and aprepitant (also known as MK-869 or L-754,030; Kramer et al., *Science* 281:1640-1645 (1998); Rupniak and Kramer, *Trends Pharmacol. Sci.* 20:1-12 (1999)) have now been shown to inhibit not only the acute but also the delayed phase of cisplatin-induced emesis in animals (Rudd et al., *Br. J. Pharmacol.* 119:931-936 (1996); Tattersall et al., *Neuropharmacology* 39:652-663 (2000)). $NK_1$ antagonists have also been demonstrated to reduce 'delayed' emesis in man in the absence of concomitant therapy (Cocquyt et al., *Eur. J. Cancer* 37:835-842 (2001); Navari et al., *N. Engl. L. Med.* 340:190-195 (1999)). When administered together with dexamethasone and 5-$HT_3$ antagonists, moreover, $NK_1$ antagonists (such as MK-869 and CJ-11,974, also known as Ezlopitant) have been shown to produce additional effects in the prevention of acute emesis (Campos et al., *J. Clin. Oncol.* 19:1759-1767 (2001); Hesketh et al., *Clin. Oncol.* 17:338-343 (1999)).

Central neurokinin $NK_1$ receptors play a major role in the regulation of emesis. $NK_1$ antagonists are active against a wide variety of emetic stimuli (Watson et al., *Br. J. Pharmacol.* 115:84-94 (1995); Tattersall et al., *Neuropharmacol.* 35:1121-1129 (1996); Megens et al., *J. Pharmacol. Exp. Ther.* 302:696-709 (2002)). The compounds are suggested to act by blocking central $NK_1$-receptors in the nucleus tractus solitarius. Apart from $NK_1$ antagonism CNS penetration is thus a prerequisite for the antiemetic activity of these compounds. Loperamide-induced emesis in ferrets can be used as a fast and reliable screening model for the antiemetic activity of $NK_1$ antagonists. Further evaluation of their therapeutic value in the treatment of both the acute and the delayed phases of cisplatin-induced emesis has been demonstrated in the established ferret model (Rudd et al., *Br. J. Pharmacol.* 119: 931-936 (1994)). This model studies both 'acute' and 'delayed' emesis after cisplatin and has been validated in terms of its sensitivity to 5-$HT_3$ receptor antagonists, glucocorticoids (Sam et al., *Eur. J. Pharmacol.* 417:231-237 (2001)) and other pharmacological challenges. It is unlikely that any future anti-emetic would find clinical acceptance unless successfully treating both the 'acute' and 'delayed' phases of emesis.

Visceral Pain and Irritable Bowel Syndrome (IBS)

Visceral sensation refers to all sensory information that originates in the viscera (heart, lungs, GI tract, hepatobiliary tract and urogenital tract), and is transmitted to the central nervous system resulting in conscious perception. Both the vagal nerve via the nodose ganglion and the primary sympathetic afferent nerves via dorsal root ganglias (DRG) and second order neurons in the dorsal horn serve as the initial pathways along which visceral sensory information is conveyed to the brain stem and to the viscero-somatic cortex. Visceral pain may be caused by neoplastic processes (e.g. pancreas cancer), inflammation (e.g. cholecystitis, peritonitis), ischemia and mechanical obstruction (e.g. urether stone).

The mainstay of medical treatment for visceral pain linked to organic disorders (in casu cancer of the viscera) still focuses on opiates.

Recent evidence suggests that non-organic visceral disorders such as irritable bowel syndrome (IBS), non-cardiac chest pain (NCCP) and chronic pelvic pain may originate from a state of "visceral hyperalgia". The latter is defined as a condition in which physiological, non-painful visceral stimuli (e.g. gut distension) lead to conscious perception of pain due to a decreased threshold for pain. Visceral hyperalgesia may reflect a state of a permanent, post-inflammatory resetting of the threshold for membrane depolarization at neuronal synapses within visceral sensory pathways. The initial inflammation may occur at the periphery (e.g. infectious gastroenteritis) or at the site of visceral sensory information integration (neurogenic inflammation in the dorsal horn). Both SP and calcitonin gene-related peptide (CGRP) have been shown to act as pro-inflammatory neuropeptides in neurogenic inflammation.

Visceral hyperalgesia is currently considered as one of the prime targets for drug development aimed at treating functional bowel diseases, which occur in 15 to 25% of the western population. They constitute an enormous socio-economic problem in terms of medical care costs, prescription costs and absenteism. Current treatment options include anti-spasmodics (IBS and NCCP), promotility agents (e.g. tegasorod in constipation-IBS), laxatives (constipation-IBS), and loperamide (diarrhea-IBS), amongst others. None of these approaches has been shown to be very effective, particularly in treating pain. Low dose tricyclic antidepressants and SSRIs are used to treat visceral hyperalgesia in pain-predominant IBS, but both classes of compounds may have considerable effects on colonic transit. Ongoing research in this field has identified a considerable number of molecular targets that could serve for drug development in visceral hyperalgesia. These include NK receptors, the CGRP receptor, 5-$HT_3$ receptors, glutamate receptors, and the kappa opioid receptor. Ideally, a "visceral analgesic compound" should block heightened sensory transfer from the viscera to the CNS without affecting the normal physiological homeostasis of the GI tract with regards to propulsive motor activity, absorption and secretion, and sensation. There is compelling evidence linking tachykinin to visceral nociceptive signalling. A number of pre-clinical publications on the role of $NK_1$, $NK_2$ and $NK_3$ receptors in visceral pain and visceral hyperalgesia indicate a discrepancy between the implication of $NK_1$, $NK_2$ and $NK_3$ receptors in the different inflammation hypersensitivity rodent models. Recently, Kamp et al., *J. Pharmacol. Exp. Ther.* 299:105-113 (2001) suggested that a combined neurokinin receptor antagonist could be more active than a selective neurokinin receptor antagonist. Substance P and $NK_1$, $NK_2$ and $NK_3$ receptors are elevated in clinical pain states, including visceral pain states (Lee et al., *Gastroenterol.* 118: A846 (2000)). Given the recent failures of $NK_1$ receptor antagonists as an analgesic in human pain trials (Goldstein et al., *Clin. Pharm. Ther.* 67:419-426 (2000)), combinations of antagonists may be necessary to have a significant clinical effect. $NK_3$ receptor antagonists are antihyperalgesic (Julia et al., *Gastroenterol.* 116:1124-1131 (1999)); *J. Pharmacol. Exp.* Ther.299:105-113 (2001)). Recently, the involvement of $NK_1$ and $NK_3$ receptors but not $NK_2$ receptors at spinal level was demonstrated in visceral hypersensitivity mediated by nociceptive and non-nociceptive afferent inputs (Gaudreau & Ploudre, *Neurosci. Lett.* 351:59-62 (2003). Combining the $NK_{1-2-3}$ antagonistic activity could therefore represent an interesting therapeutic target for the development of novel treatments for visceral hyperalgesia.

A reasonable number of pre-clinical publications over the role of $NK_1$ receptors in visceral pain has been published. Using $NK_1$ receptor knockout mice and $NK_1$ antagonists in animal models, different groups have demonstrated the important role played by the $NK_1$ receptor in hyperalgesia and visceral pain. The distribution of $NK_1$ receptors and substance P favors a major role in visceral rather than in somatic pain. Indeed more than 80% of visceral primary afferent contain substance P compared with only 25% skin afferents. $NK_1$ receptors are also involved in gastrointestinal motility (Tonini et al., *Gastroenterol.* 120:938-945 (2001); Okano et al., *J. Pharmacol. Exp. Ther.* 298:559-564 (2001)). Because of this dual role in both gastrointestinal motility and in nociception, $NK_1$ antagonists are considered to have potential to ameliorate symptoms in IBS patients.

Urinary Incontinence

Urge urinary incontinence is caused by urinary bladder or detrusor hyperreflexia ("irritable bladder"). This hyperreflexia relates to hyperexcitability of bladder sensory afferent C-fibers projecting to the spinal cord. The origin of C-fiber hyperexcitability is multifactorial but occurs for example after bladder infection and chronic distention of the bladder wall (eg. benign prostate hypertrophy, BPH). Hence, treatment should be aimed at decreasing neuronal hyperexcitability. Intravesical instillation of vanilloids (eg. capsaicin) results in a long-term beneficial effect on detrusor hyperreflexia refractory to conventional treatment with anticholinergic drugs. Analogous to animal studies, the effect of vanilloids is mediated through a neurotoxic effect on sensory nerve terminals. In human bladder, subendothelial sensory nerves contain tachykinins, which drive detrusor hyperexcitability. The NK receptors involved in this effect are peripheral $NK_2$ receptors and to a lesser extent, also $NK_1$ receptors. The latter are claimed to play a role in bladder hyperreflexia at the level of the spinal cord. As a consequence, a centrally acting $NK_1$/peripherally acting $NK_2$ antagonist is preferred for the treatment of detrusor hyperexcitability. Interestingly, activation of $NK_2$ receptors increases aromatase activity in Sertoli cells. $NK_2$ receptor antagonists reduce serum testosterone levels in mice, and this may be of therapeutic importance in BPH.

BACKGROUND PRIOR ART

Compounds containing a piperidinyl-moiety, substituted by a piperidinyl or pyrrolidinyl-moiety were published in WO97/24324 (Jul. 10, 1997), WO 97/24350 (Jul. 10, 1997) and WO97/24356 (Jul. 10, 1997), all by Janssen Pharmaceutica N. V. for use as substance P (neurokinin) antagonists. Compounds comprising a substituted diaza-spiro[4.5]decanyl-moiety were published in WO01/94346 (Dec. 13, 2001) by F. Hoffmann-La Roche AG for use as neurokinin receptor antagonists.

The compounds of the present invention differ structurally from the compounds of the prior art in that the compounds of the present invention all comprise a piperidinyl-moiety substituted with a diaza-spiro[5.5]undecanyl moiety as well as in their improved ability as potent, orally and centrally active neurokinin antagonists with therapeutic value, especially for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, COPD and micturition disorders such as urinary incontinence.

DESCRIPTION OF THE INVENTION

The present invention relates to novel substituted diazaspiro-[5.5]-undecane derivatives according to the general Formula (I)

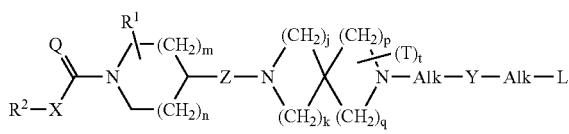

the pharmaceutically acceptable acid or base addition salts thereof, the stereochemically isomeric forms thereof, the N-oxide form thereof and prodrugs thereof, wherein:

$R^2$ is $Ar^2$, $Ar^2$-alkyl, di($Ar^2$)alkyl, $Het^1$ or $Het^1$-alkyl;

X is a covalent bond or a bivalent radical of formula —O—, —S— or —$NR^3$—;

Q is O or $NR^3$;

each $R^3$ independently from each other, is hydrogen or alkyl;

$R^1$ is selected from the group of $Ar^1$, $Ar^1$-alkyl and di($Ar^1$)-alkyl;

n is an integer, equal to 0, 1 or 2;

m is an integer, equal to 1 or 2, provided that if m is 2, then n is 1;

Z is a covalent bond or a bivalent radical of formula —$CH_2$— or >C(=O);

j, k, p, q are integers, independently from each other equal to 0, 1, 2, 3 or 4; provided that each of (j+k) and (p+q) is equal to 4;

T is =O in an alpha-position relative to the N-atom and t is an integer, equal to 0 or 1;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more, phenyl, halo, cyano, hydroxy, formyl and amino radicals;

Y is a covalent bond or a bivalent radical of formula —C(=O)—, —$SO_2$—>C=CH—R or >C=N—R, wherein R is H, CN or nitro;

L is selected from the group of hydrogen, alkyl, alkenyl, alkyloxy, alkyloxyalkyloxy, alkylcarbonyloxy, alkyloxycarbonyl, mono- and di(alkyl)amino, mono- and di(alkyloxycarbonyl)amino, mono- and di(alkylcarbonyl)amino, mono-and di($Ar^3$)amino, mono-and di($Ar^3$alkyl)amino, mono-and di($Het^2$)amino, mono-and di($Het^2$alkyl)amino, alkylsulfanyl, norbornyl, adamantyl, tricycloundecyl, $Ar^3$, $Ar^3$-oxy, $Ar^3$carbonyl, $Het^2$, Het-oxy, $Het^2$carbonyl and mono- and di($Het^2$carbonyl)amino;

$Ar^1$ is phenyl, optionally substituted with 1, 2 or 3 substituents, each independently from each other, selected from the group of halo, alkyl, cyano, aminocarbonyl and alkyloxy;

$Ar^2$ is naphthalenyl or phenyl, each optionally substituted with 1, 2 or 3 substituents, each independently from each other, selected from the group of halo, nitro, amino, mono- and di(alkyl)amino, cyano, alkyl, hydroxy, alkyloxy, carboxyl, alkyloxycarbonyl, aminocarbonyl and mono- and di(alkyl)aminocarbonyl;

$Ar^3$ is naphthalenyl or phenyl, optionally substituted with 1, 2 or 3 substituents, each independently from each other, selected from the group of alkyloxy, alkylcarbonylamino, methanesulfonyl, $Ar^1$carbonyloxyalkyl, $Ar^1$alkyloxycarbonyl, $Ar^1$alkyloxyalkyl, alkyl, halo, hydroxy, pyridinyl, morpholinyl, pyrrolyl, pyrrolidinyl, imidazo[1,2-α]pyridinyl, morpholinylcarbonyl, pyrrolidinylcarbonyl, amino and cyano;

$Het^1$ is a monocyclic heterocyclic radical selected from the the group of pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl, benzothienyl, indanyl and chromenyl; wherein each mono- and bicyclic heterocyclic radical may optionally be substituted on any atom by one or more radicals, each independently from each other, selected from the group of halo, oxo and alkyl;

$Het^2$ is a monocyclic heterocyclic radical selected from the group of pyrrolidinyl, dihydro-2H-pyranyl, pyranyl, dioxolyl, imidazolidinyl, tetrahydropyridinyl, tetrahydropyrimidinyl, pyrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrazolinyl, pyrrolyl, imidazolyl, pyrazolyl, triazolyl, furanyl, thienyl, oxazolyl, dioxazolyl, oxazolidinyl, isoxazolyl, thiazolyl, thiadiazolyl, isothiazolyl, pyridinyl, 1H-pyridinyl, pyrimidinyl, pyrazinyl, pyridazinyl, triazinyl and tetrazolyl;

or a bicyclic heterocyclic radical selected from the group of 2,3-dihydro-benzo[1,4]dioxine, octahydro-benzo[1,4]dioxine, octabicycloheptyl, benzopiperidinyl, quinolinyl, quinoxalinyl, indolyl, isoindolyl, chromanyl, benzimidazolyl, imidazo[1,2-α]pyridinyl, benzoxazolyl, benzodioxolyl, benzisoxazolyl, benzoxadiazolyl, benzothiazolyl, benzisothiazolyl, benzofuranyl, dihydroisobenzofuranyl, or benzothienyl; wherein each mono-, and bicyclic heterocyclic radical may optionally be substituted on any atom with one or more radicals selected from the group of $Ar^1$, $Ar^1$alkyl, $Ar^1$alkyloxyalkyl, halo, hydroxy, alkyl, piperidinyl, pyrrolyl, thienyl, oxo, alkyloxy, alkylcarbonyl, $Ar^1$carbonyl, mono- and di(alkyl)aminoalkyl, alkyloxyalkyl and alkyloxycarbonyl;

alkyl is a straight or branched saturated hydrocarbon radical having from 1 to 6 carbon atoms or a cyclic saturated hydrocarbon radicals having from 3 to 6 carbon atoms; each hydrocarbon radical optionally substituted on one or more carbon atoms with one or more radicals selected from the group of phenyl, halo, trihalomethyl, aminocarbonyl, methyl, ethyl, propyl, isopropyl, t-butyl, cyano, oxo, hydroxy, formyl and amino; and alkenyl is a straight or branched unsaturated hydrocarbon radical having from 1 to 6 carbon atoms and having 1 or more unsaturated bonds; or a cyclic unsaturated hydrocarbon radical having from 3 to 6 carbon atoms and having 1 or more unsaturated bonds; each hydrocarbon radical optionally substituted on one or more carbon atoms with one or more radicals selected from the group of phenyl, halo, cyano, oxo, hydroxy, formyl and amino.

More in particular, the invention relates to a compound according to the general Formula (I), the pharmaceutically acceptable acid or base addition salts thereof, the stereochemically isomeric forms thereof, the N-oxide form thereof and a prodrug thereof, wherein:

$R^2$ is $Ar^2$, $Ar^2$-alkyl or $Het^1$;

X is a covalent bond;

Q is O;

R¹ is Ar¹-alkyl;

n is an integer, equal to 1;

m is an integer, equal to 1;

Z is a covalent bond or a bivalent radical of formula —CH$_2$— or >C(=O);

j, k, p, q are integers, independently from each other equal to 1, 2 or 3 ; provided that (j+k) and (p+q) are equal to 4;

t is an integer, equal to 0 or 1;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted with an hydroxy radical;

Y is a covalent bond or a bivalent radical of formula —C(=O)— or —SO$_2$—;

L is selected from the group of hydrogen, alkyl, alkenyl, alkyloxy, norbornyl, tricycloundecyl, Ar³, Ar³-oxy, Het² and mono- and di(Het²carbonyl)amino;

Ar¹ is phenyl, optionally substituted with 2 halo-radicals;

Ar² is naphthalenyl or phenyl, each optionally substituted with 1, 2 or 3 substituents, each independently from each other, selected from the group of halo, cyano, alkyl and alkyloxy;

Ar³ is phenyl, optionally substituted with 1 substituent, selected from the group of alkyloxy, alkylcarbonylamino, methanesulfonyl, alkyl, halo, pyrrolyl and cyano;

Het¹ is a monocyclic heterocyclic radical selected from the the group of pyrrolyl, furanyl, thienyl, pyridinyl and pyrazinyl; or a bicyclic heterocyclic radical selected from the group of quinolinyl and indolyl;
    wherein each mono- and bicyclic heterocyclic radical may optionally be substituted on any atom by one or more alkyl radicals;

Het² is a monocyclic heterocyclic radical selected from the group of pyrrolidinyl, dihydro-2H-pyranyl, pyranyl, tetrahydropyridinyl, tetrahydropyrimidinyl, pyrrolyl, imidazolyl, furanyl, thienyl, oxazolidinyl, isoxazolyl, thiadiazolyl, pyridinyl, 1H-pyridinyl, pyrazinyl, pyridazinyl and tetrazolyl;
    or a bicyclic heterocyclic radical selected from the group of octabicycloheptyl, quinoxalinyl, benzimidazolyl, benzodioxolyl, benzoxadiazolyl, benzofuranyl or dihydroisobenzofuranyl; wherein each mono- and bicyclic heterocyclic radical may optionally be substituted on any atom with one or more radicals selected from the group of halo, alkyl, oxo and alkyloxycarbonyl;

alkyl is a straight or branched saturated hydrocarbon radical having from 1 to 6 carbon atoms or a cyclic saturated hydrocarbon radicals having from 3 to 6 carbon atoms; each hydrocarbon radical optionally substituted on one or more carbon atoms with one or more radicals selected from the group of trihalomethyl, aminocarbonyl, methyl, t-butyl and cyano, and alkenyl is a cyclic unsaturated hydrocarbon radical having from 3 to 6 carbon atoms and having 1 unsaturated bond.

More in particular, the invention relates to a compound according to the general Formula (I), the pharmaceutically acceptable acid or base addition salts thereof, the stereochemically isomeric forms thereof, the N-oxide form thereof and a prodrug thereof, wherein the spiro-moiety has one of the following chemical formulas (f1)-(f9), wherein all variables are defined as in Formula (I) and "a" denotes the piperidinyl-moiety of Formula (I) and "b" denotes the Alk-Y-Alk-L-moiety of Formula (I):

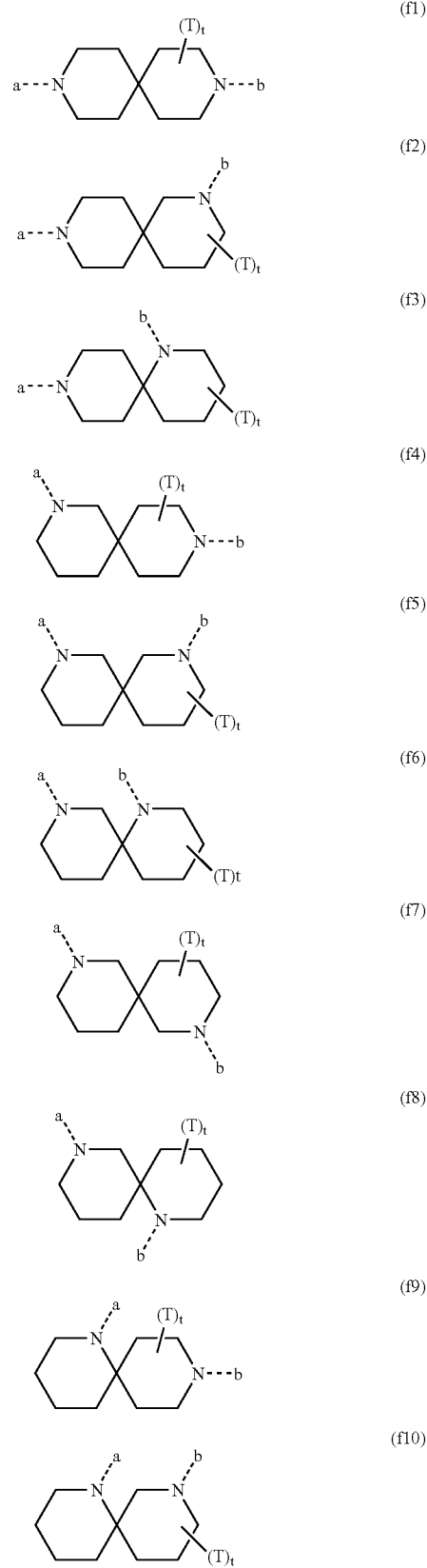

-continued

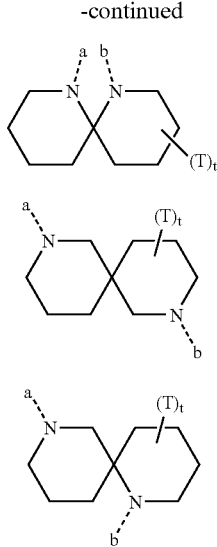

(f11)

(f12)

(f13)

More in particular, the invention relates to a compound according to the general Formula (I), the pharmaceutically acceptable acid or base addition salts thereof, the stereochemically isomeric forms thereof, the N-oxide form thereof and a prodrug thereof, wherein the spiro-moiety has the Formula (f1) (wherein j, k, p and q are equal to 2), f2 (wherein j and k are equal to 2; and p is equal to 1 and q is equal to 3) and f12 (wherein j and q are equal to 1 and k and p are equal to 3).

More in particular, the-invention relates to a compound according to the general Formula (I), the pharmaceutically acceptable acid or base addition salts thereof, the stereochemically isomeric forms thereof, the N-oxide form thereof and a prodrug thereof, wherein $R^1$ is $Ar^1$methyl and attached to the 2-position or $R^1$ is $Ar^1$ and attached to the 3-position, as exemplified in either of the following formulas for compounds according to Formula (I) wherein m and n are equal to 1 and Ar is an unsubstituted phenyl. Preferably, $Ar^1$methyl is a benzyl radical.

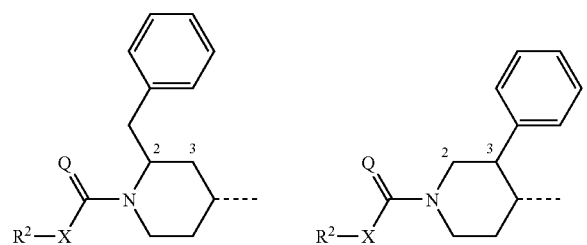

More in particular, the invention relates to a compound according to the general Formula (I), the pharmaceutically acceptable acid or base addition salts thereof, the stereochemically isomeric forms thereof, the N-oxide form thereof and a prodrug thereof, wherein the $R^2$—X—C(=Q)- moiety is 3,5-di-(trifluoromethyl)phenylcarbonyl.

More in particular, the invention relates to a compound according to the general Formula (I), the pharmaceutically acceptable acid or base addition salts thereof, the stereochemically isomeric forms thereof, the N-oxide form thereof and a prodrug thereof, wherein m and n are both equal to 1.

More in particular, the invention relates to a compound according to the general Formula (I), the pharmaceutically acceptable acid or base addition salts thereof, the stereochemically isomeric forms thereof, the N-oxide form thereof and a prodrug thereof, wherein Y is —C(=O)—.

More in particular, the invention relates to a compound according to the general Formula (I), the pharmaceutically acceptable acid or base addition salts thereof, the stereochemically isomeric forms thereof, the N-oxide form thereof and a prodrug thereof, wherein Alk is a covalent bond or —CH$_2$—.

More in particular, the invention relates to a compound according to the general Formula (I), the pharmaceutically acceptable acid or base addition salts thereof, the stereochemically isomeric forms thereof, the N-oxide form thereof and a prodrug thereof, wherein L is cyclopropyl.

More in particular, the invention relates to a compound according to the general Formula (I), the pharmaceutically acceptable acid or base addition salts thereof, the stereochemically isomeric forms thereof, the N-oxide form thereof and a prodrug thereof, wherein the compound is a compound with compound number 132, 100, 92, 93, 3, 4 and 119, as described in any one of Tables 1-7 further in this application.

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, alkenyl is defined as a monovalent straight or branched unsaturated hydrocarbon radical having from 1 to 6 carbon atoms and having 1 or more unsaturated bonds, for example methenyl, ethenyl, propenyl, butenyl, 1-methylpropenyl, 1,1-dimethylethenyl, pentenyl and hexenyl; alkenyl further defines a monovalent cyclic unsaturated hydrocarbon radical having from 3 to 6 carbon atoms and having 1 or more unsaturated bonds, for example cyclopropenyl, methyl-cyclopropenyl, cyclobutenyl, cyclopentenyl and cyclohexenyl. The definition of alkenyl also comprises an alkenyl radical that is optionally substituted on one or more carbon atoms with one or more radicals selected from the group of phenyl, halo, cyano, oxo, hydroxy, formyl and amino radicals, for example hydroxyalkenyl, in particular hydroxyethenyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, especially in the moiety Alk$^a$-Y-Alk$^b$ in Formula (I), when two or more consecutive elements of said moiety denote a covalent bond, then a single covalent bond is denoted. For example, when Alk$^a$ and Y denote both a covalent bond and Alk$^b$ is —CH$_2$—, then the moiety Alk$^a$-Y-Alk$^b$ denotes —CH$_2$—. Similarly, if Alk$^a$, Y and Alk$^b$ each denote a covalent bond and L denotes H, then the moiety Alk$^a$-Y-Alk$^b$-L denotes —H.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g of the piperazinyl or pyrrolidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with possibly the same effects.

The compounds according to the invention possess at least 2 oxydizable nitrogens (tertiary amines moieties). It is therefore highly likely that N-oxides will form in the human metabolism.

The compounds of Formula (I) may be converted to the corresponding N-oxide forms following art-known procedures for converting a trivalent nitrogen into its N-oxide form. Said N-oxidation reaction may generally be carried out by reacting the staring material of Formula (I) with an appropriate organic or inorganic-peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms having that designation, said mixtures containing all diastereomers and enantiomers of the basic molecular structure. More in particular, stereogenic centers may have the R— or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. R* and S* each indicate optically pure stereogenic centers with undetermined absolute configuration. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

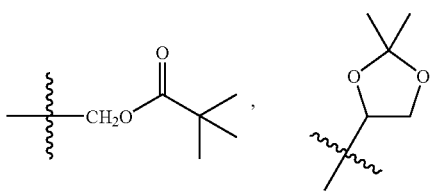

Amidated groups include groups of the formula —CONR$^y$R$^x$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

Substance P and other tachykinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the NK$_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1):5-23 (1995) and Longmore J. et al., "Neurokinin Receptors" *Pharmacological Reviews* 46(4):551-599 (1994)).

The compounds of the present invention are potent inhibitors of neurokinin-mediated effects, in particular those mediated via the NK$_1$, NK$_2$ and NK$_3$ receptor, and may therefore be described as neurokinin antagonists, especially as substance P antagonists, as may be indicated in vitro by the antagonism of substance P-induced relaxation of pig coronary arteries. The binding affinity of the present compounds for the human, guinea-pig and gerbil neurokinin receptors may also be determined in vitro in a receptor binding test using $^3$H-substance-P as radioligand. The subject compounds also show substance-P antagonistic activity in vivo as may be evidenced by, for instance, the antagonism of substance P-induced plasma extravasation in guinea-pigs, or the antagonism of drug-induced emesis in ferrets (Watson et al., *Br. J. Pharmacol.* 115:84-94 (1995)).

In view of their capability to antagonize the actions of tachykinins by blocking the neurokinin receptors, and in particular by blocking the NK$_1$, NK$_2$ and NK$_3$ receptor, the compounds according to the invention are useful as a medicine, in particular in the prophylactic and therapeutic treatment of tachykinin-mediated conditions. In particular are compounds according to the invention are useful as orally active, centrally penetrating medicines in the prophylactic and therapeutic treatment of tachykinin-mediated conditions.

More in particular, it has been found that some compounds exhibit a combined NK$_1$/NK$_2$ antagonistic activity, a combined NK$_1$/NK$_3$ antagonistic activity or a combined NK$_1$/NK$_2$/NK$_3$ antagonistic activity—as can be seen from Table 10 in the experimental section.

The invention therefore relates to a compound according to the general Formula (I), the pharmaceutically acceptable acid or base addition salts thereof, the stereochemically isomeric forms thereof, the N-oxide form thereof and prodrugs thereof, for use as a medicine.

The invention also relates to the use of a compound according to the general Formula (I), the pharmaceutically acceptable acid or base addition salts thereof, the stereochemically isomeric forms thereof, the N-oxide form thereof and prodrugs thereof for the manufacture of a medicament for treating, either prophylactic or therapeutic or both, tachykinin mediated conditions.

The compounds according to the invention are useful in the treatment of CNS disorders, in particular schizoaffective disorders, depression, anxiety disorders, stress-related disorders, sleep disorders, cognitive disorders, personality disorders, eating disorders, neurodegenerative diseases, addiction disorders, mood disorders, sexual dysfunction, visceral pain and other CNS-related conditions; inflammation; allergic disorders; emesis; gastrointestinal disorders, in particular irritable bowel syndrome (IBS); skin disorders; vasospastic diseases; fibrosing and collagen diseases; disorders related to immune enhancement or suppression and rheumatic diseases and body weight control.

In particular, the compounds according to the invention are useful in the treatment or prevention of schizoaffective disorders resulting from various causes, including schizoaffective disorders of the manic type, of the depressive type, of mixed type; paranoid, disorganized, catatonic, undifferentiated and residual schizophrenia; schizophreniform disorder; delusional disorder; brief psychotic disorder; shared psychotic disorder; substance-induced psychotic disorder; and psychotic disorder not otherwise specified.

In particular, the compounds according to the invention are useful in the treatment or prevention of depression including but not limited to major depressive disorders including bipolar depression; unipolar depression; single or recurrent major depressive episodes with or without psychotic features, catatonic features, melancholic features, atypical features or postpartum onset, and, in the case of recurrent episodes, with or without seasonal pattern. Other mood disorders encompassed within the term "major depressive disorder" include dysthymic disorder with early or late onset and with or without atypical features, bipolar I disorder, bipolar II disorder, cyclothymic disorder, recurrent brief depressive disorder, mixed affective disorder, neurotic depression, post traumatic stress disorder and social phobia; dementia of the Alzheimer's type with early or late onset, with depressed mood; vascular dementia with depressed mood; substance-induced mood disorders such as mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

In particular, the compounds according to the invention are useful in the treatment or prevention of anxiety disorders, including but not limited to panic attack; agoraphobia; panic disorder without agoraphobia; agoraphobia without history of panic disorder; specific phobia; social phobia; obsessive-compulsive disorder; post-traumatic stress disorder; acute stress disorder; generalized anxiety disorder; anxiety disorder due to a general medical condition; substance-induced anxiety disorder; and anxiety disorder not otherwise specified.

In particular, the compounds according to the invention are useful in the treatment or prevention of stress-related disorders associated with depression and/or anxiety, including but not limited to acute stress reaction; adjustment disorders, such as brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct and adjustment disorders with other specified predominant symptoms; and other reactions to severe stress.

In particular, the compounds according to the invention are useful in the treatment or prevention of sleep disorders, including but not limited to dysomnia and/or parasomnias as primary sleep disorders; insomnia; sleep apnea; narcolepsy; circadian rhythms disorders; sleep disorders related to another mental disorder; sleep disorder due to a general medical condition; and substance-induced sleep disorder.

In particular, the compounds according to the invention are useful in the treatment or prevention of cognitive disorders, including but not limited to dementia; amnesic disorders and cognitive disorders not otherwise specified, especially dementia caused by degenerative disorders, lesions, trauma, infections, vascular disorders, toxins, anoxia, vitamin deficiency or endocrinic disorders; dementia of the Alzheimer's type, with early or late onset, with depressed mood; AIDS-associated dementia or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III. Furthermore, the compounds according to the invention are also useful as memory and/or cognition enhancers in healthy humans with no cognitive and/or memory deficit.

In particular, the compounds according to the invention are useful in the treatment or prevention of personality disorders, including but not limited to paranoid personality disorder; schizoid personality disorder; schizotypical personality disorder; antisocial personality disorder; borderline personality disorder; histrionic personality disorder; narcissistic personality disorder; avoidant personality disorder; dependent personality disorder; obsessive-compulsive personality disorder and personality disorder not otherwise specified.

In particular, the compounds according to the invention are also useful in the treatment or prevention of eating disorders, including anorexia nervosa; atypical anorexia nervosa; bulimia nervosa; atypical bulimia nervosa; overeating associated with other psychological disturbances; vomiting associated with other psychological disturbances; and non-specified eating disorders.

In particular, the compounds according to the invention are also useful in the treatment or prevention of neurodegenerative diseases, including but not limited to Alzheimer's disease; Huntington's chorea; Creutzfeld-Jacob disease; Pick's disease; demyelinating disorders, such as multiple sclerosis and ALS; other neuropathies and neuralgia; multiple sclerosis; amyotropical lateral sclerosis; stroke and head trauma.

In particular, the compounds according to the invention are also useful in the treatment or prevention of addiction disorders, including but not limited to substance dependence or abuse with or without physiological dependence, particularly where the substance is alcohol, amphetamines, amphetamine-like substances, caffeine, cocaine, hallucinogens, inhalants, nicotine, opioids (such as cannabis, heroin and morphine), phencyclidine, phencyclidine-like compounds, sedative-hypnotics, benzodiazepines and/or other substances, particularly useful for treating withdrawal from the above substances and alcohol withdrawal delirium.

In particular, the compounds according to the invention are also useful in the treatment or prevention of mood disorders induced particularly by alcohol, amphetamines, caffeine, cannabis, cocaine, hallucinogens, inhalants, nicotine, opioids, phencyclidine, sedatives, hypnotics, anxiolytics and other substances.

In particular, the compounds according to the invention are also useful in the treatment or prevention of sexual dysfunction, including but not limited to sexual desire disorders; sexual arousal disorders; orgasmic disorders; sexual pain disorders; sexual dysfunction due to a general medical condition; substance-induced sexual dysfunction and sexual dysfunction not otherwise specified.

In particular, the compounds according to the invention are also useful in the treatment or prevention of pain, including but not limited to traumatic pain such as postoperative pain; traumatic avulsion pain such as brachial plexus; chronic pain such as arthritic pain such as occurring in osteo-rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy and phantom limb pain; various forms of headache such as migraine, acute or chronic tension headache, temporomandibular pain, maxillary sinus pain and cluster headache; odontalgia; cancer pain; visceral pain; gastrointestinal pain; nerve entrapment pain; sport's injury pain; dysmennorrhoea; menstrual pain; meningitis; arachnoiditis; musculoskeletal pain; low back pain such as spinal stenosis, prolapsed disc, sciatica, angina, ankylosing spondyolitis; gout; burns; scar pain; itch; and thalamic pain such as post stroke thalamic pain.

In particular, the compounds according to the invention are also useful in the treatment or prevention of the following other CNS-related conditions: akinesia, alinetic-rigid syndromes, dyskinesia and medication-induced parkinsonism, Gilles de la Tourette syndrome and its symptoms, tremor, chorea, myoclonus, tics and dystonia, attention-deficit/hyperactivity disorder (ADHD), Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification, behavioral disturbances and conduct disorders in dementia and the mentally retarded, including restlessness and agitation, extra-pyramidal movement disorders, Down's syndrome and Akathisia.

In particular, the compounds according to the invention are also useful in the treatment or prevention of inflammation, including but not limited to inflammatory conditions in asthma, influenza, chronic bronchitis and rheumatoid arthritis; inflammatory conditions in the gastrointestinal tract such as, but not limited to Crohn's disease, ulcerative colitis, inflammatory bowel disease and non-steroidal anti-inflammatory drug induced damage; inflammatory conditions of the skin such as herpes and eczema; inflammatory conditions of the bladder such as cystitis and urge incontinence; eye and dental inflammation and pancreatitis, in particular chronic and acute pancreatitis.

In particular, the compounds according to the invention are also useful in the treatment or prevention of allergic disorders, including but not limited to allergic disorders of the skin such as but not limited to urticaria; and allergic disorders of the airways such as but not limited to rhinitis.

In particular, the compounds according to the invention are also useful in the treatment or prevention of emesis, i.e. nausea, retching and vomiting, including but not limited to acute emesis, delayed emesis and anticipatory emesis; emesis induced by drugs such as cancer chemotherapeutic agents such as alkylating agents, for example cyclophosphamide, carmustine, lomustine and chlorambucil; cytotoxic antibiotics, for example dactinomycin, doxorubicin, mitomycin-C and bleomycin; anti-metabolites, for example cytarabine, methotrexate and 5-fluorouracil; vinca alkaloids, for example etoposide, vinblastine and vincristine; and other drugs such as cisplatin, dacarbazine, procarbazine and hydroxyurea; and combinations thereof; radiation sickness; radiation therapy, such as in the treatment of cancer; poisons; toxins such as toxins caused by metabolic disorders or by infection, such as gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, such as myocardial infarction or peritonitis; migraine; increased intracranial pressure; decreased intracranial pressure (such as altitude sickness); opioid analgesics, such as morphine; gastro-oesophageal reflux disease; acid indigestion; over-indulgence of food or drink; acid stomach; sour stomach; waterbrash/regurgitation; heartburn, such as episodic heartburn, nocturnal heartburn and meal induced heartburn; and dyspepsia.

In particular, the compounds according to the invention are also useful in the treatment or prevention of gastrointestinal disorders, including but not limited to irritable bowel syndrome (IBS), skin disorders such as psoriasis, pruritis and sunburn; vasospastic diseases such as angina, vascular headache and Reynaud's disease, cerebral ischaemia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; cough; and body weight control, including obesity.

Most in particular, the compounds according to the invention are also useful for the manufacture of a medicament for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence.

The present invention also relates to a method for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence, comprising administering to a human in need of such administration an effective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a pro-drug thereof.

The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally, mainly centrally active $NK_1$, $NK_1/NK_2$, $NK_1/NK_3$ and $NK_1/NK_2/NK_3$ antagonists, pharmaceutical compositions comprising said compounds for administration orally are especially advantageous.

Synthesis

The compounds according to the invention can generally be prepared by a succession of steps, each of which is known to the skilled person.

The final compounds of Formula (Ia) are conveniently prepared by reductively N-alkylating an intermediate compound of Formula (II) with an intermediate compound of Formula (III). Said reductive N-alkylation may be performed in a reaction-inert solvent such as, for example, dichloromethane, ethanol or toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium (IV)isopropylate as described in J. Org. Chem, 1990, 55, 2552-2554. Using said complex-forming agent may also result in an improved cis/trans ratio in favor of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

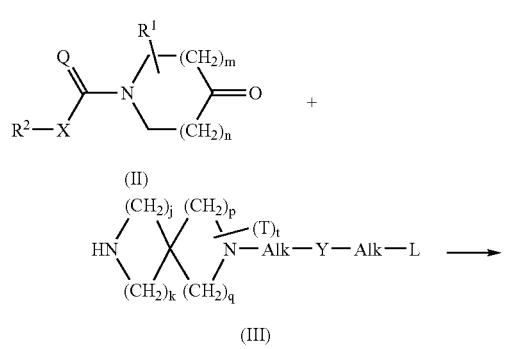

(II)

(III)

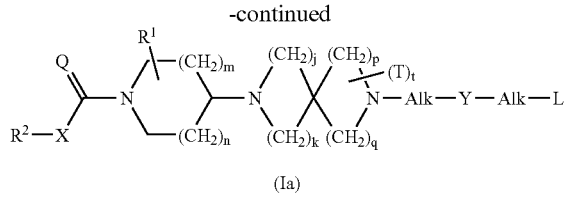

(Ia)

In this and the following preparations, the reaction products may be isolated from the reaction medium and, if necessary, further purified according to methodologies generally known in the art such as, for example, extraction, crystallization, trituration and chromatography.

The final compounds of Formula (Ib) are conveniently prepared by reductively N-alkylating an intermediate compound of Formula (V) with an intermediate compound of Formula (III). Said reductive N-alkylation may be performed in a reaction-inert solvent such as, for example, dichloromethane, ethanol or toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium (IV)iso-propylate as described in J. Org. Chem, 1990, 55, 2552-2554. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

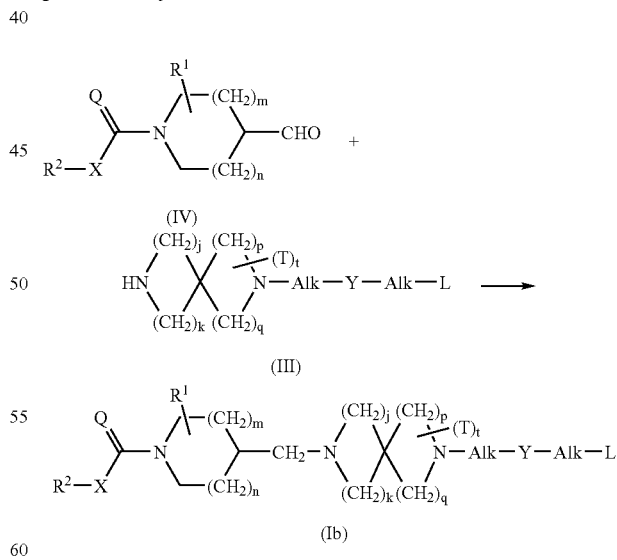

The final compounds of Formula (Ic) are conveniently prepared by reacting a carboxylic acid compound of Formula (V) with an intermediate compound of Formula (III). The reaction can be performed in a reaction-inert solvent such as, for example, a chlorinated hydrocarbon, e.g. dichloromethane, in the presence of a suitable base such as, for example, sodium carbonate, sodium hydrogen carbonate or triethylamine and in the presence of an activator, such as e.g. DCC (dicyclohexylcarbodiimide), CDI (carbonyldiimidazole) and EDCI (1-(3-dimethylaminopropyl)-3-ethylcarbodiimide.HCl). Stirring may enhance the rate of the reaction. The reaction may conveniently be carried out at a temperature ranging between room temperature and reflux temperature.

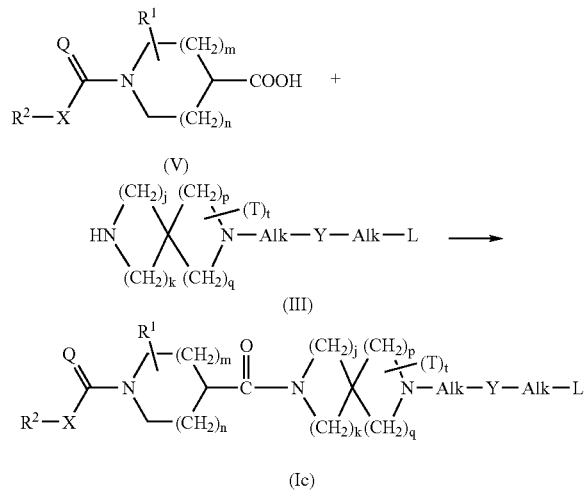

Especially advantageous is the preparation of a final compound according to any of Formulas (Ia), (Ib) and (Ic) and according to the previously mentioned reaction schemes wherein a compound according to Formula (II), (IV) or (V) is reacted with a compound according to Formula (III) in which the Alk-Y-Alk-L-moiety is benzyl (Formula (XI)), thus giving rise to a compound wherein the Alk-Y-Alk-L-moiety is benzyl. Said final compound is pharmacologically active and can be converted into a final compound according to Formula (I') in which the Alk-Y-Alk-L-moiety is hydrogen by reductive hydrogenation using e.g. hydrogen as a reducing agent in combination with a suitable catalyst such as, for example, palladium-on-charcoal or platinum-on-charcoal. The resulting final compound according to the invention can then be converted into other compounds according to Formula (I) by art-known transformations, e.g. acylation and alkylation.

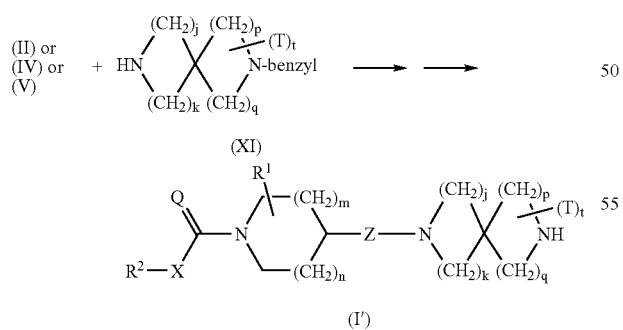

In particular, the final compounds of Formula (Id) can be prepared by reacting a final compound of Formula (I') with an intermediate compound of Formula (VI) wherein $W^1$ is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

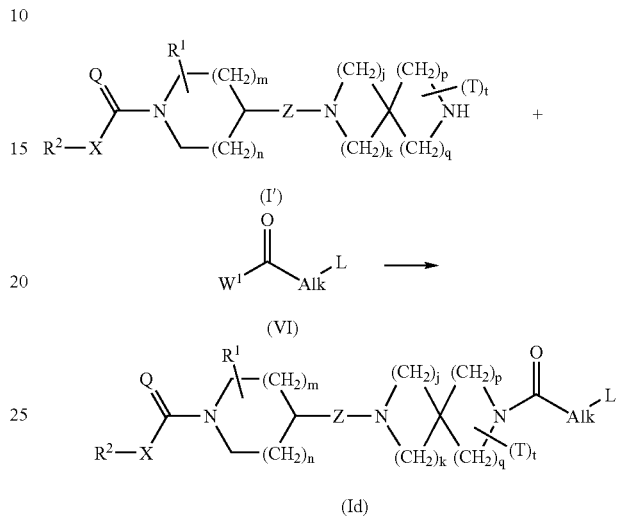

Alternatively, the final compounds of Formula (Id) can also be prepared by reacting a final compound of Formula (I') with a carboxylic acid of Formula (VII). The reaction can be performed in a reaction-inert solvent such as, for example, a chlorinated hydrocarbon, e.g. dichloromethane, in the presence of a suitable base such as, for example, sodium carbonate, sodium hydrogen carbonate or triethylamine and in the presence of an activator, such as e.g. DCC (dicyclohexylcarbodiimide), CDI (carbonyl-diimidazole) and EDCI (1-(3-dimethylaminopropyl)-3-ethylcarbodiimide. HCl). Stirring may enhance the rate of the reaction. The reaction may conveniently be carried out at a temperature ranging between room temperature and reflux temperature.

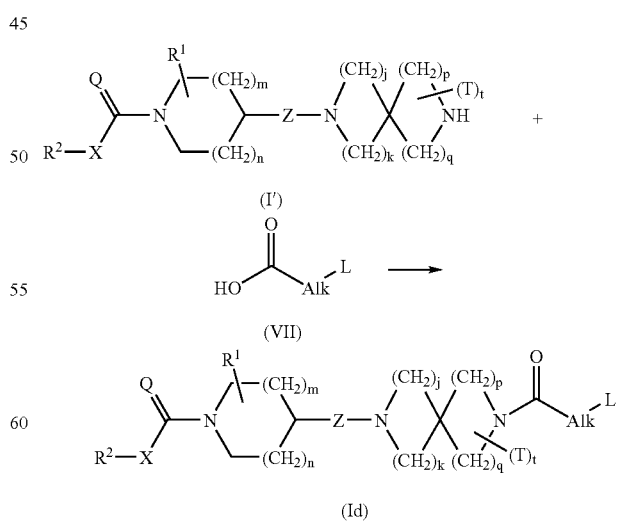

The final compounds of Formula (Ie) can be prepared by alkylation of a final compound of Formula (I') with compound of Formula (VIII) wherein W² in Formula (VIII) is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

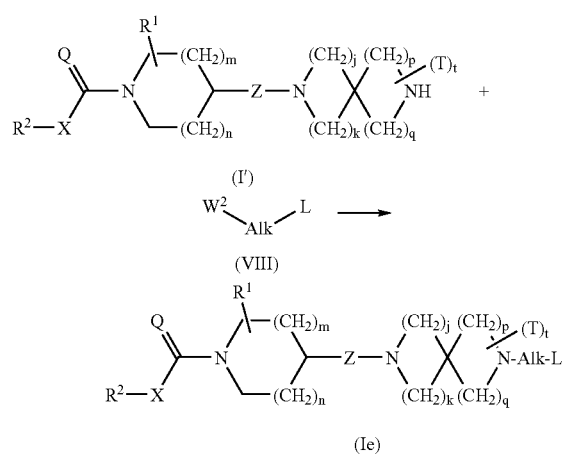

The final compounds of Formula (If) can be prepared by reductively N-alkylating an intermediate compound of Formula (I') with an intermediate compound of Formula (IX). Said reductive N-alkylation may be performed in a reaction-inert solvent such as, for example, dichloromethane, ethanol or toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium(IV)isopropylate as described in J. Org. Chem, 1990, 55, 2552-2554. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydro-genation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

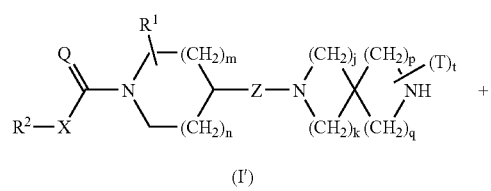

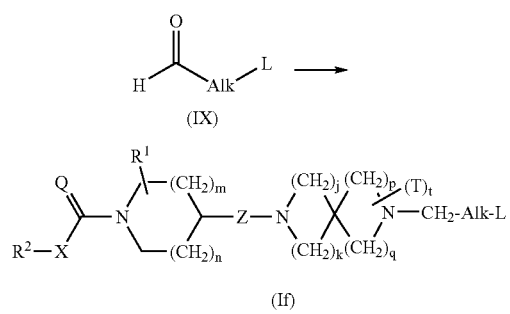

The final compounds of formula (Ig) are conveniently prepared by a Boronic Mannich reaction as described in Tetrahedron, 1997, 53, 16463-16470; J. Am. Chem. Soc. 1998, 120, 11798-11799 or Tetrahedron Letters, 2002, 43, 5965-5968 with an intermediate compound of Formula (I') and intermediate compounds (X) and (XI) wherein Y in formula (X) is a bivalent radical of formula —CH₂— or >C(=O) and W³ in Formula (XI) is hydrogen or an alkyl chain. Said Boronic Mannich reaction may be reacted in the manner of a one-pot reaction with a carbohydrate or its dimer of Formula (X) and an arylboronic acid or arylboronic ester of Formula (XI) in a reaction-inert solvent such as, for example, dichloromethane, ethanol, or 2,2,2-trifluoroethanol or a mixture thereof. Stirring may enhance the rate of the reaction. The reaction may conveniently be carried out at a temperature ranging between room temperature and reflux temperature.

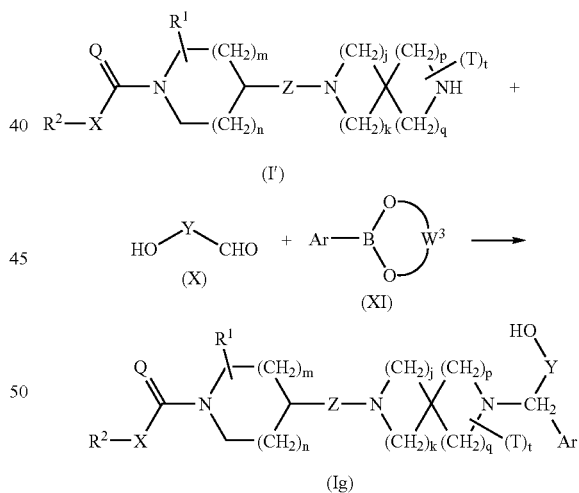

The following examples are intended to illustrate but not to limit the scope of the present invention.

Experimental Part

Hereinafter "RT" means room temperature, "CDI" means 1,1'-carbonyldiimidazole, "DIPE" means diisopropylether, "MIK" means methyl isobutyl keton, "BINAP" means [1,1'-binaphthalene]-2,2'-diylbis[diphenylphosphine], "NMP" means 1-methyl-2-pyrrolidinone, "Pd₂(dba)₃" means tris(dibenzylideneacetone)dipalladium, "DMF" means N,N-dimethylformamide, "EDCI" means 1-ethyl-3-(3-dimethy lamino-propyl)carbodiimide hydrochloride and "HOBT" means hydroxybenzotriazole.

Preparation of the Intermediate Compounds

EXAMPLE A1 a. Preparation of Intermediate Compound 1

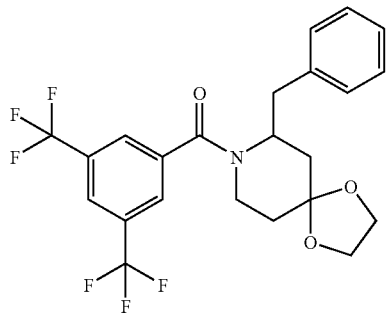

Et$_3$N (0.55 mol) was added to a stirring mixture of 7-(phenylmethyl)-1,4-dioxa-8-azaspiro[4.5]decane (0.5 mol) in toluene (1500 ml). 3,5-Bis(trifluoromethyl)benzoyl chloride (0.5 mol) was added over a 1-hour period (exothermic reaction). The mixture was stirred at room temperature for 2 hours, then allowed to stand for the weekend and washed three times with water (500 ml, 2×250 ml). The organic layer was separated, dried, filtered and the solvent was evaporated. Yield: 245 g (100%). Crystallization of 2 gram of this fraction from petroleum ether yielded 1 g of intermediate compound 1. (50%).

b. Preparation of Intermediate Compound 2

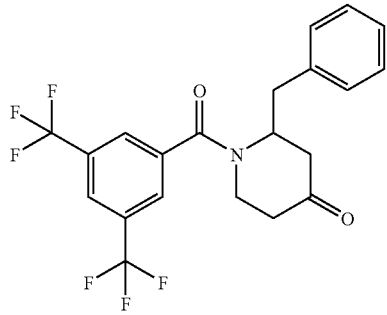

HCl cp (300 ml) was added to a mixture of intermediate compound 1 (0.5 mol) in ethanol (300 ml) and H$_2$O (300 ml). The reaction mixture was stirred at 60° C. for 20 hours. The precipitate was filtered off, ground, stirred in H$_2$O, filtered off, washed with petroleum ether and dried. Yield: 192 g of intermediate compound 2 ((±)-1-[3,5-bis(trifluoromethyl) benzoyl]-2-(phenylmethyl)-4-piperidinone) (89.4 %) (mixture of R and S enantiomers).

c. Preparation of Intermediate Compound 3 and Intermediate Compound 4

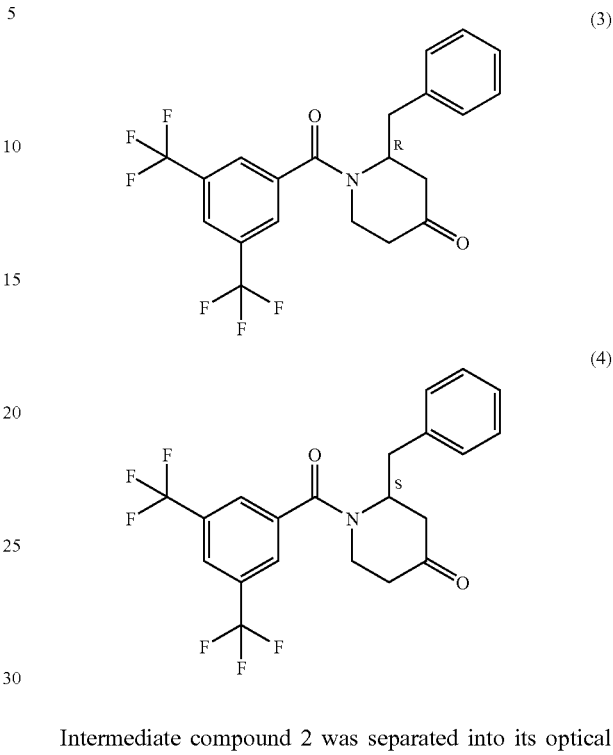

Intermediate compound 2 was separated into its optical isomers by chiral column chromatography over Chiralpak (CHIRALPAK AS 1000 Å 20 mm (DAICEL); eluent: hexane/2-propanol 70/30). Two product fractions were collected and each solvent was evaporated. Yield Fraction 1: 32.6 g of intermediate compound 3 (R), and Fraction 2: 30.4 g of intermediate compound 4 (S).

EXAMPLE A2 a. Preparation of Intermediate Compound 5

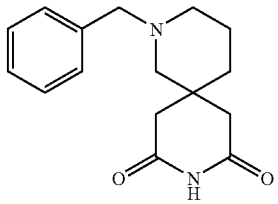

A mixture of 1-(phenylmethyl)-4,4-piperidinediacetic acid .hydrochloride (0.214 mol) and urea (0.149 mol) was stirred at 180° C. for 1 hour. EtOH and satured NaHCO$_3$ were added. The precipitate was filtered off and dried. EtOH was evaporated. The mixture was extracted with CH$_2$Cl$_2$. The organic layer was separated, dried (MgSO$_4$), filtered, and the solvent was evaporated. The residue (20 g) was purified by column chromatography over silica gel (eluent: CH$_2$Cl$_2$/CH$_3$OH/ NH$_4$OH 99/1/0.1; 20-45 µm). Two fractions were collected and the solvent was evaporated. Yield: 4.4 g of intermediate compound 5.

a. Preparation of Intermediate Compound 6

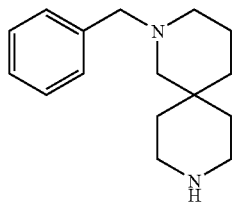

LiAlH₄ (0.463 mol) was added portionwise at 5° C. to THF (400 ml). Intermediate compound 5 (0.077 mol) was added portionwise. The mixture was stirred at 5° C. for 15 minutes, then brought to room temperature and stirred and refluxed for 8 hours. Cold H₂O was added slowly. The mixture was filtered over celite. Celite was washed with CH₂Cl₂. The filtrate was extracted with CH₂Cl₂. The organic layer was separated dried (MgSO₄), filtered, and the solvent was evaporated. Yield: 13.7 g of intermediate compound 6 (72%).

EXAMPLE A3 a. Preparation of Intermediate Compound 7

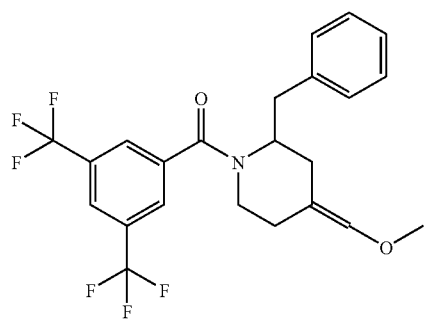

Reaction under N₂ atmosphere. A mixture of (methoxymethyl)triphenylphosphonium chloride (0.0055 mol) and N-(1-methylethyl)-2-propanamine (0.0083 mol) in dry THF, p.a. (20 ml) was stirred at −70° C. 2.5 M BuLi/hexane (0.0055 mol) was added dropwise. More 2.5 M BuLi/hexane (2.2 ml) was added. The mixture was allowed to warm to room temperature. The reaction mixture was stirred for 30 min at 20° C. The mixture was re-cooled to −25° C. A solution of intermediate compound 3 (prepared according to A1.c) (0.005 mol) in some dry THF, p.a. was added dropwise and the reaction mixture was allowed to warm to room temperature. The reaction mixture was stirred overnight at room temperature, then decomposed with water. The organic solvent was evaporated and the aqueous concentrate was extracted with CH₂Cl₂. The separated organic layer was dried, filtered and the solvent evaporated. The residue was purified over silica gel (eluent: CH₂Cl₂). The desired fractions were collected and the solvent was evaporated. Yield: 1.30 g intermediate compound 7 (57%).

b. Preparation of Intermediate Compound 8

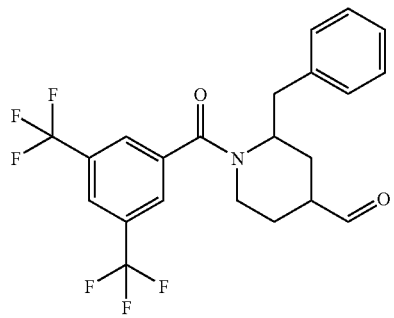

A mixture of intermediate compound 7 (0.0028 mol) in 1.6N HCl (6 ml) and THF (6 ml) was stirred for one hour at 40° C. The THF was evaporated and the aqueous concentrate was extracted with CH₂Cl₂. The separated organic layer was washed with an aqueous Na₂CO₃ solution, dried, filtered and the solvent evaporated. Yield: 1.24 g of intermediate compound 8 (100%, used in next reaction step, without further purification).

c. Preparation of Intermediate Compound 9

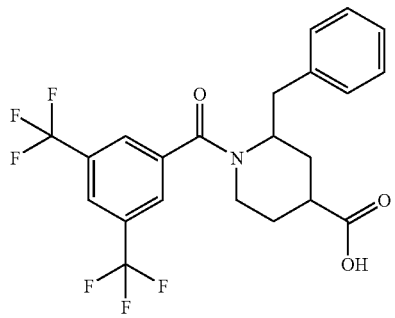

A mixture of intermediate compound 8 (0.0081 mol) in CH₃CN (p.a.) (20 ml) was stirred on an ice bath, giving mixture (I). A mixture of NaOCl₂ (0.00975 mol) dissolved in H₂O (20 ml) was added dropwise at <10° C. to mixture (I). The reaction mixture was stirred for 2 hours at <10° C. and was stirred overnight at room temperature. NaOH (25 ml, 10%) was added dropwise to the mixture at room temperature and the reaction mixture was washed with DEPE (2 times). The aqueous layer was acidified with HCl (10%) at <10° C., then extracted with CH₂Cl₂. The organic layer was dried (MgSO₄) and filtered off. The solvent was evaporated and the residue was crystallised from DIPE. Yield: 3.0 g of intermediate compound 9 (80%).

EXAMPLE A4 a. Preparation of Intermediate Compound 10

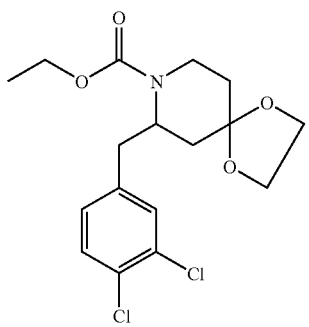

A mixture of 2-[(3,4-dichlorophenyl)methyl]-4-oxo-1-piperidinecarboxylic acid ethyl ester (0.3 mol), 1,2-ethanediol (1.5 mol) and 4-methylbezenesulfonic acid (2 g) in toluene (750 ml) was stirred and refluxed for 68 hours using a water separator. The solvent was evaporated. The residue was partitioned between water and toluene. The organic layer was separated, washed with water, dried, filtered and the solvent evaporated. Yield: 113.5 g of intermediate compound 10.

b. Preparation of Intermediate Compound 11

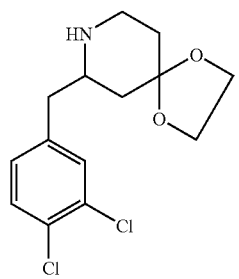

A mixture of intermediate compound 10 (prepared according to A4.a) (0.1 mol) and KOH (0.9 mol) in 2-propanol (500 ml) was stirred and refluxed overnight. The solvent was evaporated. The residue was dissolved in $CH_2Cl_2$ and then washed with a small amount of $H_2O$. The organic layer was dried, filtered and the solvent was evaporated. Yield: 33 g of intermediate compound 11.

c. Preparation of Intermediate Compound 12 and 13

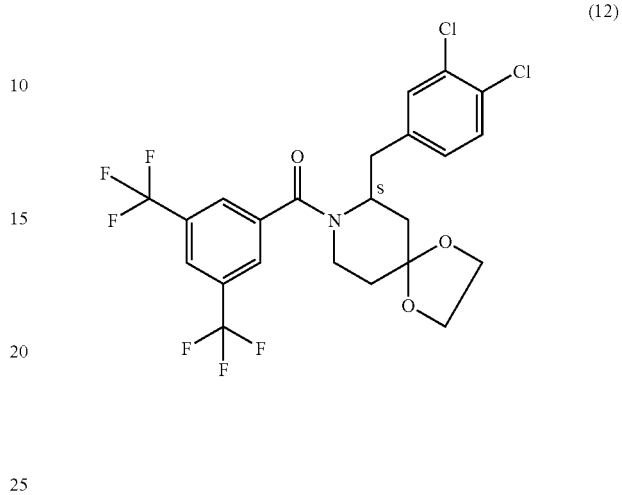

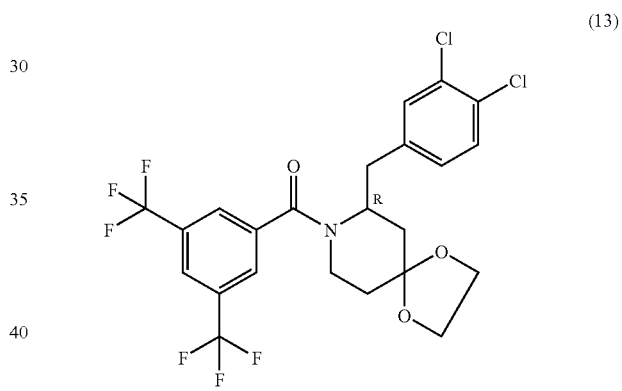

Intermediate compound 11 (prepared according to A4.b) (0.139 mol) was dissolved in $CH_2Cl$ (420 ml). 3,5-Bis(trifluoromethyl)benzoyl chloride (0.15 mol) was added dropwise. $CH_2Cl_2$ (30 ml) was added. The reaction mixture was stirred for 2 hours at room temperature. The reaction mixture was washed with 50% NaOH, with water, then dried, filtered and the solvent evaporated. The residue was purified over silica gel (eluent gradient: $CH_2Cl_2/CH_3OH$ from 100/0 to 95/5). The product fractions were collected and the solvent was evaporated. The residue was crystallized from DIPE, filtered off and dried. Yield: 56.3 g of fraction 1. The filtrate was evaporated The residue was suspended in petroleum ether, filtered off and dried. Yield: 9 g of fraction 2. The fractions were separated and purified by chiral column chromatography (AD, 3-g injections; eluent: heptane/ethanol 95/5). Two product fraction groups were collected and their solvent was evaporated. Each residue was crystallized from DIPE, filtered off and dried. Yield: 23.9 g of intermediate compound 12 and 28.5 g of intermediate compound 13.

d. Preparation of Intermediate Compound 14

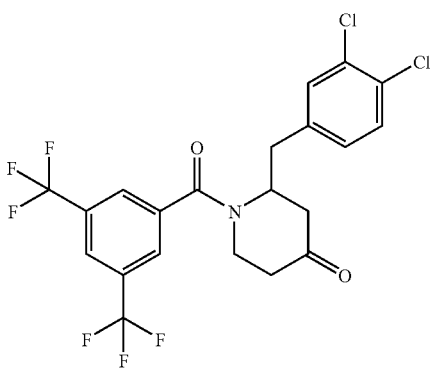

A mixture of intermediate compound 12 (prepared according to A4.c) (0.0424 mol) in HCl (6N) (230 ml) was stirred and refluxed for 4 hours, then the reaction mixture was stirred overnight and extracted with CH₂Cl₂. The organic layer was separated, washed with water, dried and the solvent was evaporated. Yield: 20 g of intermediate compound 14.

EXAMPLE A5 a. Preparation of Intermediate Compound 15

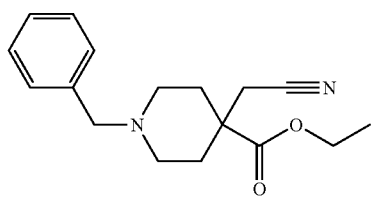

A solution of ethyl acetate (0.22 mol) in THF (200 ml) was added at −78° C. to a solution of nBuLi, 1.6M (0.178 mol) and diisopropylamine (0.1365 mol) in THF (100 ml) under N₂ flow. The mixture was stirred for 30 minutes. A solution of

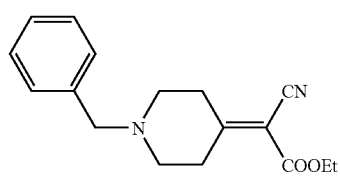

(prepared according to the teachings in *Helvetica Chimica Acta*, (1972), 55(7), p 2432-8 of which the content is included herein)) (0.105 mol) in THF (300 ml) was added at −78° C. The mixture was stirred for 2 hours. H₂O was added. The mixture was extracted with EtOAc. The organic layer was separated, dried (MgSO₄), filtered, and the solvent was evaporated. The residue (60 g) was purified by column chromatography over silica gel (eluent: cyclohexane/EtOAc 60/40). The pure fractions were collected and the solvent was evaporated. Yield: 9.8 g intermediate compound 15 (25%).

b. Preparation of Intermediate Compound 16

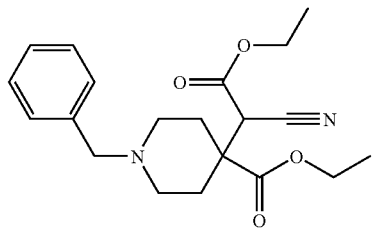

A mixture of intermediate compound 15 (0.026 mol) and LiCl(0.052 mol) in DMSO (100 ml) and H₂O (10 ml) was stirred at 200° C. for 2 hours. H₂O was added. The mixture was extracted with EtOAc. The organic layer was separated, dried (MgSO₄), filtered, and the solvent was evaporated. The residue (10 g) was purified by column chromatography over silica gel (eluent: cyclohexane/EtOAc 60/40; 15-40 μm). The pure fractions were collected and the solvent was evaporated. Yield: 6.7 g of intermediate compound 16 (86%).

c. Preparation of Intermediate Compound 17

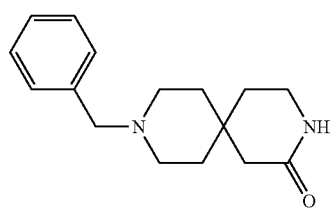

A mixture of intermediate compound 16 (0.022 mol) and NiRa (6.7 g) in CH₃OH (100 ml) was hydrogenated at room temperature overnight under a 3 bar pressure, then filtered over celite. The filtrate was evaporated. The residue (7.5 g) was purified by column chromatography over silica gel (eluent gradient: CH₂Cl₂/CH₃OH/NH₄OH 98/2/0 to 85/15/1). Yield 2.7 g (46%).

d. Preparation of Intermediate Compound 18

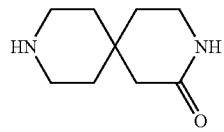

A mixture of intermediate compound 17 (0.0104 mol) and Pd/C (0.3 g) in CH₃OH (30 ml) was hydrogenated at 50° C. overnight under a 4 bar pressure, then filtered over celite. Celite was washed with CH₂Cl₂. The filtrate was evaporated Yield: 1.9 g of intermediate compound 18 (100%).

Preparation of the Final Compounds

EXAMPLE B1 a. Preparation of Final Compound 1

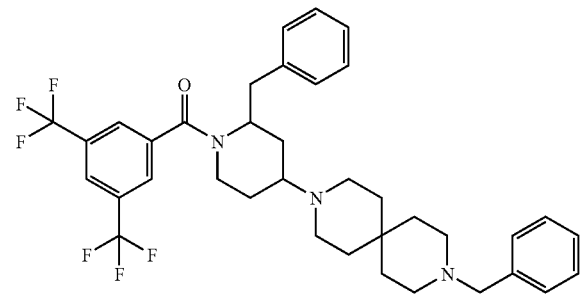

A mixture of intermediate compound 3 (prepared according to A1.c) (0.02 mol), 3-(phenylmethyl)-3,9-diazaspiro-[5.5]-undecane (0.02 mol) and Ti(iPrO)$_4$ (0.035 mol) in 1,2-dichloroethane (80 ml) was stirred at 50° C. for a overnight, then brought to room temperature under N$_2$ flow. NaBH(OAc)$_3$ (0.035 mol) was added portionwise. The mixture was stirred at room temperature for 8 hours and poured out on ice. K$_2$CO$_3$ 10% was added. The mixture was filtered over celite and washed with CH$_2$Cl$_2$. The filtrate was extracted with CH$_2$Cl$_2$. The organic layer was separated, dried (MgSO$_4$), filtered, and the solvent was evaporated. The residue (26 g) was purified by column chromatography over silica gel (eluent gradient: CH$_2$Cl$_2$/CH$_3$OH/NH$_4$OH 95/5/0.5 to 90/10/1; 20-45 μm). Three fractions were collected and the solvent was evaporated.

Yield: 1.8 g of final compound 1 (15%).

b. Preparation of Final Compound 5

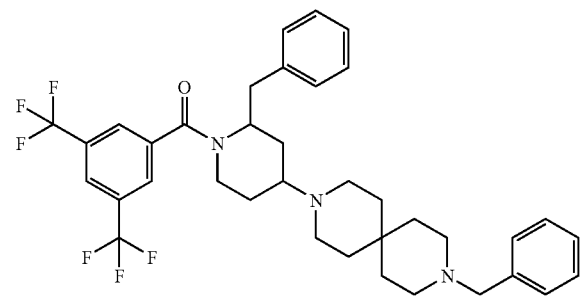

A mixture of intermediate compound 3 (prepared according to A1.c) (0.033 mol), 3-(phenylmethyl)-3,9-diazaspiro-[5.5]-undecane (0.033 mol), Ti(iPrO)$_4$ (0.036 mol) and Pd/C (1.5 g) in thiophene (1 ml) and methanol (150 ml) was hydrogenated at 50° C. for 18 hours under a 5 bar pressure, then filtered over celite. Celite was washed with CH$_3$OH. The filtrate was evaporated till dryness. The residue was dissolved in CH$_2$Cl$_2$. K$_2$CO$_3$ 10% was added. The mixture was stirred at room temperature for 30 minutes, then filtered over celite. Celite was washed with CH$_2$Cl$_2$. The filtrate was extracted with CH$_2$Cl$_2$. The organic layer was separated, dried (MgSO$_4$), filtered, and the solvent was evaporated. The residue (20 g) was purified by column chromatography over silica gel (eluent: CH$_2$Cl$_2$/CH$_3$OH/NF$_4$OH 94/6/0.5; 20-45 μm). Two fractions were collected and the solvent was evaporated. The residue was dissolved in iPrOH and converted into the hydrochloric acid salt. The precipitate was filtered off and dried.

Yield: 3.5 g of final compound 5 (14%) (melting point: 183° C.).

c. Preparation of Final Compound 2

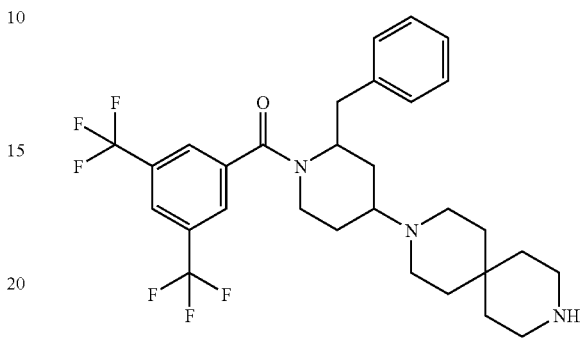

A mixture of final compound 1 (prepared according to B1.a) (0.001 mol) and Pd/C (0.1 g) in CH$_3$OH (6 ml) was hydrogenated at 40° C. for 48 hours under a 3 bar pressure, then filtered over celite. Celite was washed with CH$_3$OH/CH$_2$Cl$_2$. The filtrate was evaporated. The residue (0.6 g) was purified by column chromatography over silica gel (eluent gradient: CH$_2$Cl$_2$/CH$_3$OH/NH$_4$OH 90/10/0.1 to 85/15/1; 35-70 μm). The pure fractions were collected and the solvent was evaporated. Yield: 0.3 g of final compound 2 (58%).

EXAMPLE B2

Preparation of Final Compound 3

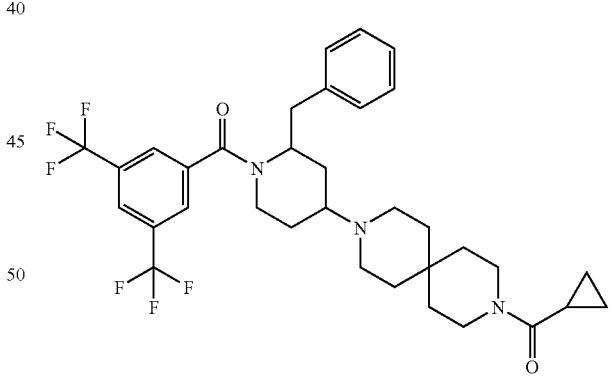

A mixture of final compound 2 (prepared according to B1.c) (0.0044 mol), cyclopropanecarboxylic acid (0.0052 mol), EDCI (0.0052 mol), HOBT (0.0058 mol) and Et$_3$N (0.0066 mol) in CH$_2$Cl$_2$ (25 ml) was stirred at room temperature for 24 hours, poured out into H$_2$O and extracted with CH$_2$Cl$_2$. The organic layer was separated, dried (MgSO$_4$), filtered, and the solvent was evaporated. The residue (3 g) was purified by column chromatography over silica gel (eluent: CH$_2$Cl$_2$/CH$_3$OH/NH$_4$OH 95/5/0.2; 15-40 μm). The pure fractions were collected and the solvent was evaporated. The residue (1.8 g, 64%) was crystallized from diethyl ether. The precipitate was filtered off and dried. Yield: 1.45 g of final compound 3 (51%) (melting point: 160° C.).

EXAMPLE B3

Preparation of Final Compound 4

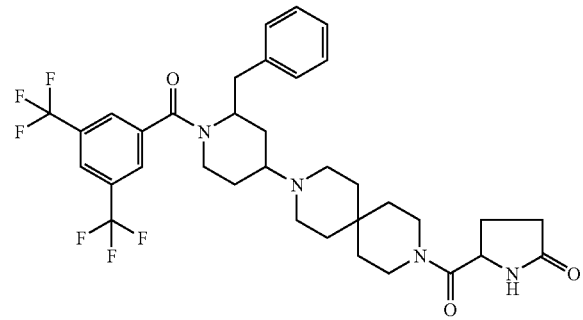

A mixture of polystyrene-carbodiimide (1 eq) in CH$_2$Cl$_2$ (5 ml) was stirred and cooled at 5° C. The acid (for the described example: alpha(hydroxymethyl)benzeneacetic acid) (1.5 eq) in CH$_2$Cl$_2$ (1 ml) was added and the mixture was stirred at room temperature for 30 minutes. A solution of final compound 2 (prepared according to B1.c) in CH$_2$Cl$_2$ (2 ml) was added and the mixture was stirred at 50° C. overnight. The reaction mixture was filtered and the solvent evaporated. The residue was purified by column chromatography over silica gel (Kromasil 5 μm, eluent gradient: CH$_2$Cl$_2$ 100 % to 95/5 CH$_2$Cl$_2$/MeOH). The pure fraction was collected yielding 71% of the final compound 4.

EXAMPLE B4

Preparation of Final Compound 92

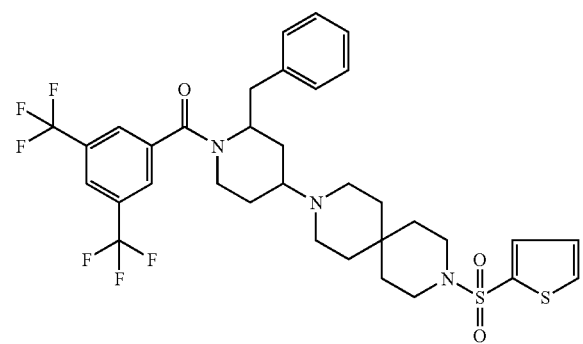

2-thiophenesulfonyl chloride (0.001 mol) was added portionwise at room temperature to a solution of final compound 2 (prepared according to B1.c) (0.001 mol) and Et$_3$N (0.001 mol) in CH$_2$Cl$_2$ (4 ml). The mixture was stirred at room temperature for 48 hours. The organic layer was washed with K$_2$CO$_3$ 10%, dried (MgSO$_4$), filtered, and the solvent was evaporated. The residue (0.45 g) was purified by column chromatography over silica gel (eluent: CH$_2$Cl$_2$/CH$_3$OH/ NH$_4$OH 97/3/0.1; 15-40 μm). The pure fractions were collected and the solvent was evaporated This fraction was dissolved in 2-propanone and converted into the ethanedioic acid salt. The precipitate was filtered off and dried. Yield: 0.28 g of compound 92 (46%) (melting point: 132° C.).

EXAMPLE B5

Preparation of Final Compound 119

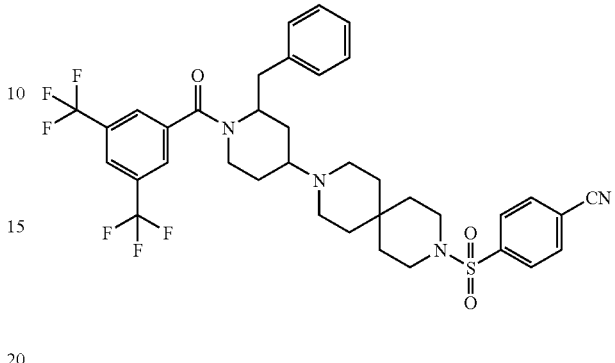

A mixture of final compound 2 (prepared according to B1.c) (0.176 mmol), 4-cyanobenzenesulfonylchloride (1.4 eq) and polymer supported morpholine (1.5 eq) in CH$_2$Cl$_2$ (2 ml) was stirred at room temperature for 24 hours. Polymer supported tris(2-aminoethyl)amine polymer bond (1 eq) was added. The mixture was stirred at room temperature for 24 hours, filtered. The residue was purified by column chromatography over silica gel (Kromasil 5 μm, eluent gradient: CH$_2$Cl$_2$ 100% to 95/5 CH$_2$Cl$_2$/MeOH). The pure fraction was collected yielding 54% of the final compound 119.

EXAMPLE B6

Preparation of Final Compound 6

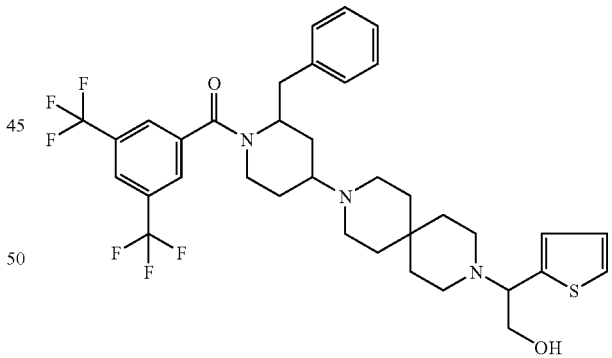

A mixture of final compound 1 (prepared according to B1.c) (0.001 mol), 2-thienylboronic acid (0.01 mol) and glycolaldehyde dimer (0.001 mol) in ethanol (5 ml) was stirred at room temperature for 18 hours. K$_2$CO$_3$ 10% was added. The mixture was extracted with EtOAc. The organic layer was separated, dried (MgSO4), filtered, and the solvent was evaporated. The residue (0.6 g) was purified by column chromatography over silica gel (eluent: CH$_2$Cl$_2$/CH$_3$OH/NH$_4$OH (95/5/0.1; 10 μm). The pure fractions were collected and the solvent was evaporated. Yield: 0.238 g of final compound 6 (42%).

EXAMPLE B7 a) Preparation of Final Compound 130

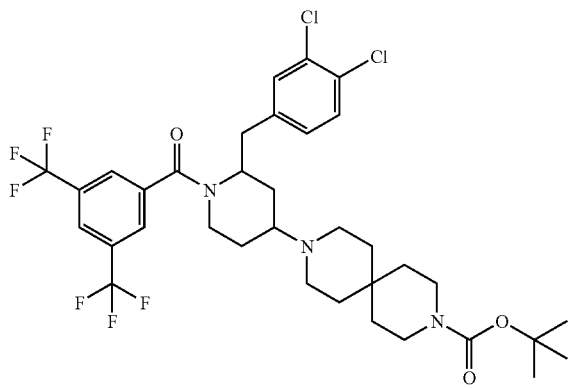

A mixture of intermediate compound 14 (prepared according to A4.d) (0.0068 mol), 1,1-dimethylethyl-3,9-diazaspiro-[5,5]-undecane-3-carboxylic acid ester (0.0075 mol) and titanium(IV)isopropylate (0.0115 mol) in 1,2-dichloroethane (50 ml) was stirred at 50° C. overnight. NaBH(OAc)$_3$ (0.0115 mol) was added. The mixture was stirred at 50° C. for 1 hour. K$_2$CO$_3$ 10% and CH$_2$Cl$_2$ were added. The mixture was filtered over celite. The organic layer was separated, dried (MgSO$_4$), filtered, and the solvent was evaporated. The residue (6.3 g) was purified by column chromatography over silica gel (eluent: CH$_2$Cl$_2$/CH$_3$OH/NH$_4$OH 97/3/0.1; 15-40 μm). Two fractions were collected and the solvent was evaporated. Yield: 0.8 g of final compound 130 (16%) (melting point: 80° C.).

b) Preparation of Final Compound 129

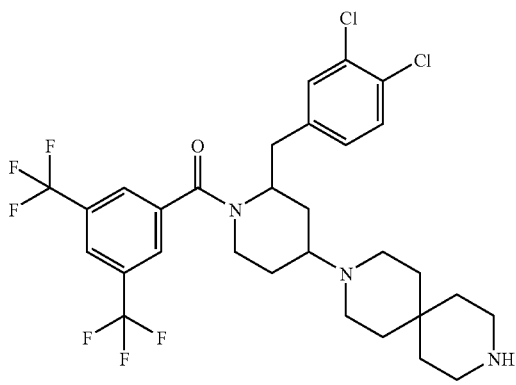

A mixture of final compound 130 (prepared according to B7.a) (0.0011 mol) in HCl in iPrOH (8 ml) and iPrOH (8 ml) was stirred at room temperature for 6 hours. H$_2$O was added. The mixture was basified with K$_2$CO$_3$ and extracted with CH$_2$Cl$_2$. The organic layer was separated, dried (MgSO$_4$), filtered, and the solvent was evaporated till dryness. Yield: 0.6 g of final compound 129 (86%).

EXAMPLE B8 a) Preparation of Final Compound 191

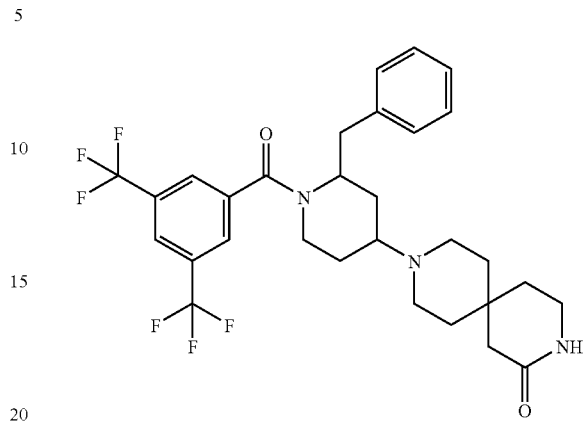

A mixture of intermediate compound 3 (prepared according to A1.c) (0.012 mol), intermediate compound 18 (prepared according to A5.d)(0.011 mol), titanium(IV)isopropylate (0.012 mol) and thiophene (0.6 g) in Pd/C (0.5 ml) and CH$_3$OH (100 ml) was hydrogenated at 50° C. under a 5 bar pressure, then filtered over celite. The filtrate was evaporated. The residue was taken up in K$_2$CO$_3$ 10% and CH$_2$Cl$_2$. The mixture was filtered over celite. The filtrate was extracted with CH$_2$Cl$_2$. The organic layer was separated, dried (MgSO$_4$), filtered, and the solvent was evaporated. The residue (6.6 g) was purified by column chromatography over silica gel (eluent: CH$_2$Cl$_2$/CH$_3$OH/NH$_4$OH 93/7/0.5; 15-40 μm). Two fractions were collected and the solvent was evaporated. Yield: 1.5 g (2R-cis) (24%) and 0.9 g (2R-trans) (14%).

b) Preparation of Final Compound 195

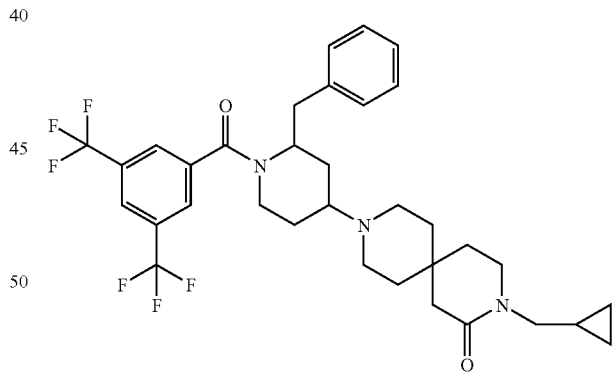

NaH (0.0007 mol) was added at 5° C. to a mixture of final compound 191 (0.0005 mol) in THF (2.5 ml) under N$_2$ flow. The mixture was stirred at 50° C. for 30 minutes. A solution of (bromomethyl)cyclopropane (0.0005 mol) in THF (2.5 ml) was added. The mixture was stirred at 60° C. overnight. H$_2$O was added. The mixture was extracted with EtOAc. The organic layer was separated, dried (MgSO$_4$), filtered, and the solvent was evaporated. The residue (0.3 g) was purified by column chromatography over kromasil (eluent gradient: CH$_2$Cl$_2$ 100 to CH$_2$Cl$_2$/CH$_3$OH/NH$_4$OH 90/10/0.5; 5 μm). The pure fractions were collected and the solvent was evaporated. Yield: 0.23 g of final compound 195 (70%).

EXAMPLE B9

Preparation of Final Compound 204

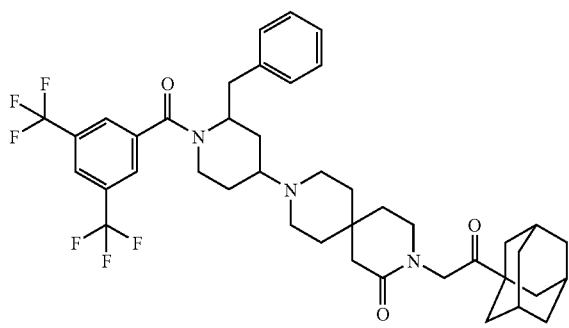

NaH was added at 5° C. to a solution of final compound 191 (prepared according to B8.a) in THF under $N_2$ flow. The mixture was stirred for 30 minutes. 1-adamantyl bromomethyl ketone was added. The mixture was stirred at 60° C. overnight.

Yield: 8% of final compound 204.

EXAMPLE B10

Preparation of Final Compound 206

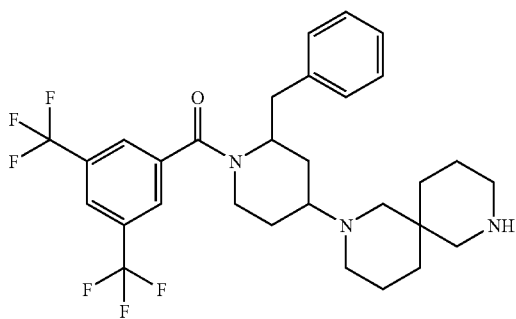

A mixture of intermediate compound 3 (prepared according to A1.c) (0.028 mol),

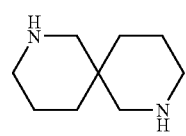

(prepared according to the teachings in CAS180-50-7, *J. Med. Chem.* 1990, 33, 2270-2275 of which the content is included herein) (0.028 mol), titanium(IV)isopropylate (0.033 mol) and Pd/C (1.5 g) in $CH_3OH$ (150 ml) was hydrogenated at 50° C. for 18 hours under a 3 bar pressure, then filtered over celite. Celite was washed with $CH_3OH$. The filtrate was evaporated till dryness. The residue was dissolved in cch. $K_2CO_3$ 10% was added. The mixture was stirred at room temperature for 1 hour, then filtered over celite. The filtrate was extracted with $CH_2Cl_2$. The organic layer was separated, dried ($MgSO_4$), filtered, and the solvent was evaporated Yield: 16 g of final compound 206 (100%). This product was used directly in the next reaction step.

EXAMPLE B11

Preparation of Final Compound 212

A mixture of final compound 206 (prepared according to B10), 3-furancarboxylic acid, PL-DCC (1.2 eq) and $Et_3N$ (1.5 eq) in THF was stirred in a sealed vessel at 100° C. in a microwaves (150 W) for 15 minutes. Yield: 11% of final compound 212.

The following compounds were made according to one of the examples above.

TABLE 1

| Comp. No. | Exp. No. | Alk^a | Y | Alk^b | L | stereo descriptors |
|---|---|---|---|---|---|---|
| 2 | B1.c | cb | cb | cb | H | 2R-trans |
| 5 | B1.a | —CH₂— | cb | cb | phenyl | 2R-cis |
| 1 | B1.a | —CH₂— | cb | cb | phenyl | 2R-trans |
| 6 | B6 | CH(CH₂OH) | cb | cb | 2-thienyl | 2R-trans |
| 7 | B2 | cb | C=O | cb | tert-butyl | 2R-trans |
| 8 | B3 | cb | C=O | cb | tert-butyl | 2R-cis |
| 10 | B3 | cb | C=O | cb | cyclopropyl | 2R-cis |
| 3 | B2 | cb | C=O | cb | cyclopropyl | 2R-trans |
| 11 | B3 | cb | C=O | cb | 1-methylcyclopropyl | 2R-trans |
| 12 | B3 | cb | C=O | cb | 1-(CF₃)cyclopropyl | 2R-trans |

TABLE 1-continued
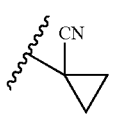
| Comp. No. | Exp. No. | Alk$^a$ | Y | Alk$^b$ | L | stereo descriptors |
|---|---|---|---|---|---|---|
| 13 | B3 | cb | C=O | cb | 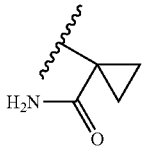 | 2R-trans |
| 14 | B3 | cb | C=O | cb | 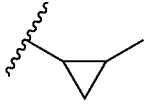 | 2R-trans |
| 15 | B3 | cb | C=O | cb | 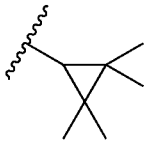 | 2R-trans |
| 16 | B3 | cb | C=O | cb | 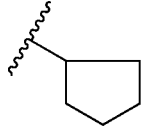 | 2R-trans |
| 17 | B3 | cb | C=O | cb | 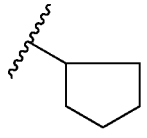 | 2R-cis |
| 18 | B3 | cb | C=O | cb | 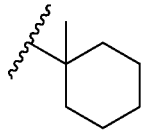 | 2R-cis |
| 37 | B3 | cb | C=O | cb | 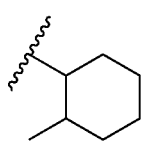 | 2R-trans |
| 38 | B3 | cb | C=O | cb |  | 2R-cis |

TABLE 1-continued
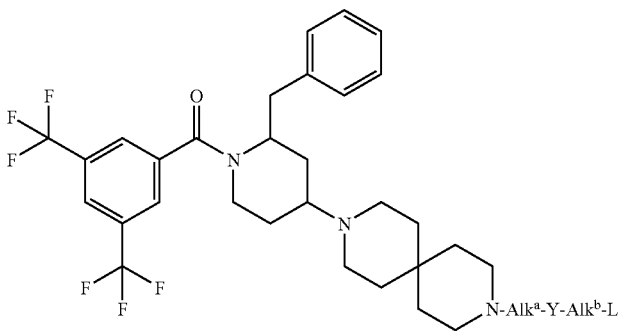
| Comp. No. | Exp. No. | Alk$^a$ | Y | Alk$^b$ | L | stereo descriptors |
|---|---|---|---|---|---|---|
| 39 | B3 | cb | C=O | cb | 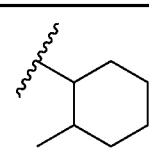 | 2R-cis |
| 40 | B3 | cb | C=O | cb | 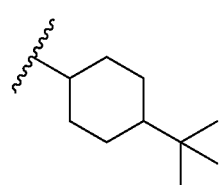 | 2R-trans |
| 41 | B3 | cb | C=O | cb | 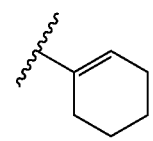 | 2R-trans |
| 19 | B3 | cb | C=O | cb | 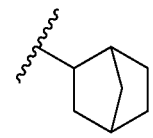 | 2R-trans |
| 59 | B3 | cb | C=O | cb | 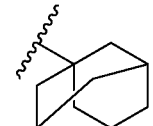 | 2R-cis |
| 60 | B3 | cb | C=O | cb | 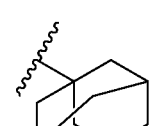 | 2R-trans |
| 20 | B3 | cb | C=O | cb | 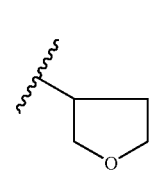 | 2R-cis |

TABLE 1-continued
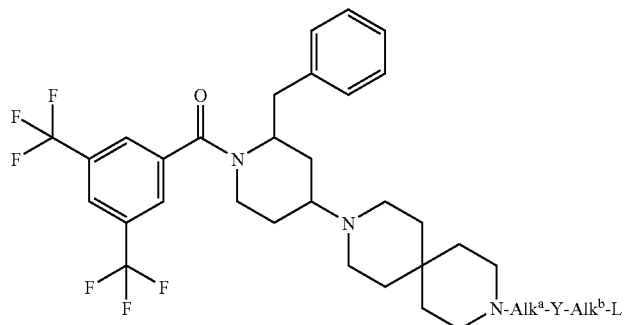
| Comp. No. | Exp. No. | Alk$^a$ | Y | Alk$^b$ | L | stereo descriptors |
|---|---|---|---|---|---|---|
| 21 | B2 | cb | C=O | cb | 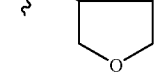 | 2R-trans; .oxalate |
| 4 | B2 + B3 | cb | C=O | cb |  | 2R-trans |
| 22 | B2 | cb | C=O | cb | 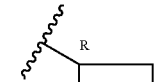 | 2R-trans |
| 23 | B3 | cb | C=O | cb |  | 2R-cis |
| 24 | B2 | cb | C=O | cb |  | 2R-trans; .oxalate |
| 25 | B3 | cb | C=O | cb |  | 2R-trans |
| 26 | B3 | cb | C=O | cb |  | 2R-cis |

TABLE 1-continued

| Comp. No. | Exp. No. | Alk$^a$ | Y | Alk$^b$ | L | stereo descriptors |
|---|---|---|---|---|---|---|
| 27 | B3 | cb | C=O | cb | 2-methylfuran-3-yl | 2R-trans |
| 28 | B3 | cb | C=O | cb | thiophen-3-yl | 2R-cis |
| 29 | B3 | cb | C=O | cb | 5-methylthiophen-2-yl | 2R-cis |
| 30 | B3 | cb | C=O | cb | 5-methylthiophen-2-yl | 2R-trans |
| 31 | B3 | cb | C=O | cb | 3-methylthiophen-2-yl | 2R-cis |
| 32 | B3 | cb | C=O | cb | 3-methylthiophen-2-yl | 2R-trans |
| 33 | B3 | cb | C=O | cb | 1-methyl-1H-pyrrol-2-yl | 2R-trans |
| 34 | B3 | cb | C=O | cb | 1-methyl-1H-imidazol-4-yl | 2R-trans |

TABLE 1-continued
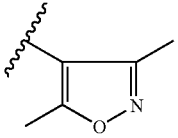
| Comp. No. | Exp. No. | Alk$^a$ | Y | Alk$^b$ | L | stereo descriptors |
|---|---|---|---|---|---|---|
| 35 | B3 | cb | C=O | cb | 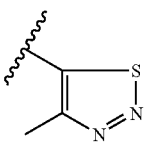 | 2R-trans |
| 36 | B3 | cb | C=O | cb | 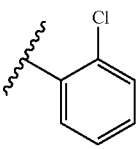 | 2R-trans |
| 42 | B3 | cb | C=O | cb | 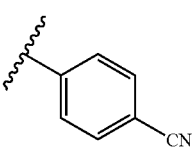 | 2R-trans; .oxalate |
| 43 | B3 | cb | C=O | cb | 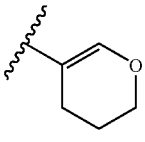 | 2R-trans |
| 44 | B3 | cb | C=O | cb | Error! Objects cannot be created from editing field codes. | 2R-trans |
| 45 | B3 | cb | C=O | cb | 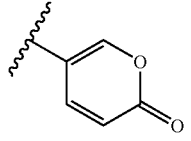 | 2R-trans |
| 46 | B3 | cb | C=O | cb | 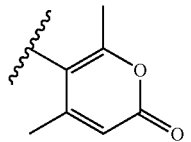 | 2R-trans |
| 47 | B3 | cb | C=O | cb | | 2R-trans |

TABLE 1-continued
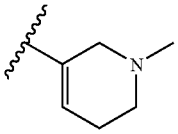
| Comp. No. | Exp. No. | Alk$^a$ | Y | Alk$^b$ | L | stereo descriptors |
|---|---|---|---|---|---|---|
| 48 | B3 | cb | C=O | cb | 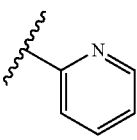 | 2R-trans |
| 49 | B3 | cb | C=O | cb | 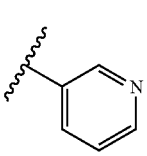 | 2R-trans |
| 50 | B3 | cb | C=O | cb | 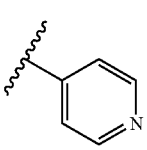 | 2R-trans |
| 51 | B3 | cb | C=O | cb | 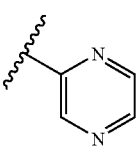 | 2R-trans |
| 52 | B3 | cb | C=O | cb | 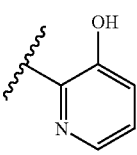 | 2R-trans |
| 53 | B3 | cb | C=O | cb | 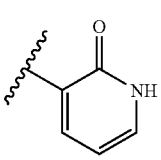 | 2R-trans |
| 54 | B3 | cb | C=O | cb | 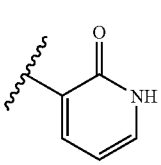 | 2R-cis |
| 55 | B3 | cb | C=O | cb | 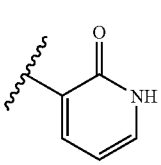 | 2R-trans |

TABLE 1-continued
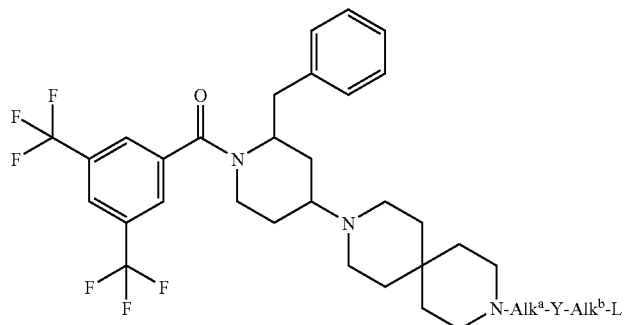
| Comp. No. | Exp. No. | Alk$^a$ | Y | Alk$^b$ | L | stereo descriptors |
|---|---|---|---|---|---|---|
| 56 | B3 | cb | C=O | cb | 3-(2-oxo-1H-pyridinyl) | 2R-cis |
| 57 | B3 | cb | C=O | cb | 5-(2-oxo-1H-pyridinyl) | 2R-trans |
| 58 | B3 | cb | C=O | cb | 4,5-dihydro-6-oxo-pyridazinyl | 2R-trans |
| 61 | B3 | cb | C=O | cb | camphanoyl | 2R-trans |
| 62 | B3 | cb | C=O | cb | 1,3-benzodioxol-5-yl | 2R-trans |
| 63 | B3 | cb | C=O | cb | 1,3-benzodioxol-5-yl | 2R-cis |
| 64 | B3 | cb | C=O | cb | benzofuran-2-yl | 2R-trans |

TABLE 1-continued
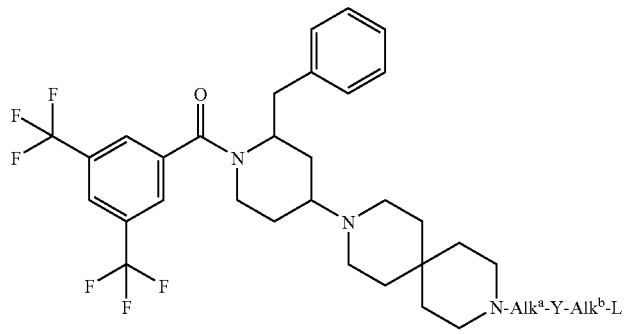
| Comp. No. | Exp. No. | Alk^a | Y | Alk^b | L | stereo descriptors |
|---|---|---|---|---|---|---|
| 65 | B3 | cb | C=O | cb | quinoxalin-2-yl | 2R-cis |
| 66 | B3 | cb | C=O | cb | quinoxalin-2-yl | 2R-trans |
| 67 | B3 | cb | C=O | cb | 2-methyl-1H-benzimidazol-5-yl | 2R-trans |
| 68 | B3 | cb | C=O | cb | benzo[1,2,5]oxadiazol-5-yl | 2R-trans |
| 69 | B3 | cb | C=O | —CH₂— | tert-butyl | 2R-trans |
| 70 | B3 | cb | C=O | —CH₂— | cyclopent-2-enyl | 2R-trans |
| 71 | B3 | cb | C=O | —CH₂— | cyclohexyl | 2R-trans |
| 72 | B3 | cb | C=O | —CH₂— | adamantyl | 2R-trans |

TABLE 1-continued
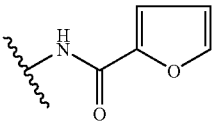
| Comp. No. | Exp. No. | Alk$^a$ | Y | Alk$^b$ | L | stereo descriptors |
|---|---|---|---|---|---|---|
| 73 | B3 | cb | C=O | —CH$_2$— | 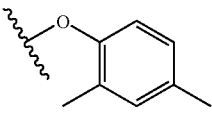 | 2R-trans |
| 74 | B3 | cb | C=O | —CH$_2$— | 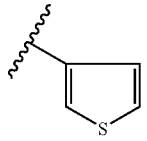 | 2R-trans |
| 75 | B3 | cb | C=O | —CH$_2$— | 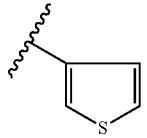 | 2R-cis |
| 76 | B3 | cb | C=O | —CH$_2$— | 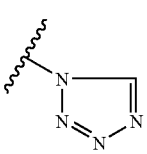 | 2R-trans |
| 77 | B3 | cb | C=O | —CH$_2$— | 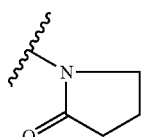 | 2R-trans |
| 78 | B3 | cb | C=O | —CH$_2$— | 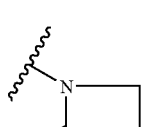 | 2R-trans |
| 79 | B3 | cb | C=O | —CH$_2$— | 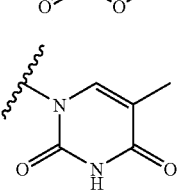 | 2R-trans |
| 80 | B3 | cb | C=O | —CH$_2$— | | 2R-trans |

TABLE 1-continued
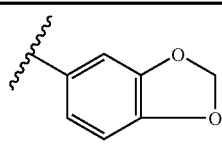
| Comp. No. | Exp. No. | Alk$^a$ | Y | Alk$^b$ | L | stereo descriptors |
|---|---|---|---|---|---|---|
| 81 | B3 | cb | C=O | —CH$_2$— | 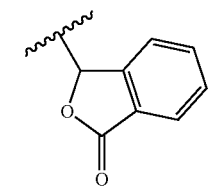 | 2R-trans |
| 82 | B3 | cb | C=O | —CH$_2$— | 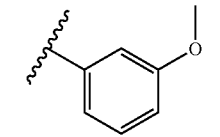 | 2R-trans |
| 83 | B3 | cb | C=O | —CH$_2$—CH$_2$— | 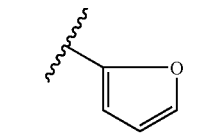 | 2R-trans |
| 84 | B3 | cb | C=O | —CH=CH— | 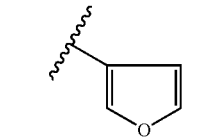 | 2R-trans |
| 85 | B3 | cb | C=O | —CH=CH— | 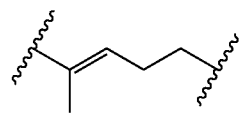 | 2R-trans |
| 9 | B3 | cb | C=O | 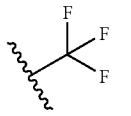 | H | 2R-trans |
| 86 | B3 | cb | C=O | 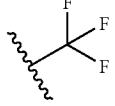 | 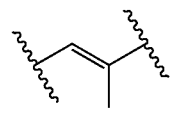 | 2R-trans |
| 87 | B3 | cb | C=O | 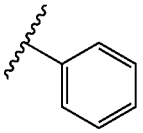 | 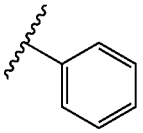 | 2R-trans |

TABLE 1-continued

| Comp. No. | Exp. No. | Alk$^a$ | Y | Alk$^b$ | L | stereo descriptors |
|---|---|---|---|---|---|---|
| 88 | B3 | cb | C=O | (CH with CH₂OH branch) | phenyl | 2R-trans |
| 89 | B3 | cb | C=O | cyclopropyl-1,1-diyl | phenyl | 2R-trans |
| 90 | B3 | cb | C=O | cyclopentyl-1,1-diyl | phenyl | 2R-trans |
| 167 | B5 | cb | O=S=O | cb | isopropyl | 2R-trans |
| 91 | B5 | cb | O=S=O | cb | CF₃ | 2R-trans |
| 92 | B4 | cb | O=S=O | cb | 2-thienyl | 2R-trans; .oxalate |
| 93 | B5 | cb | O=S=O | cb | 3-thienyl | 2R-trans |
| 94 | B5 | cb | O=S=O | cb | 5-chloro-2-thienyl | 2R-trans |

TABLE 1-continued

| Comp. No. | Exp. No. | Alk$^a$ | Y | Alk$^b$ | L | stereo descriptors |
|---|---|---|---|---|---|---|
| 95 | B5 | cb | O=S(=O) | cb | 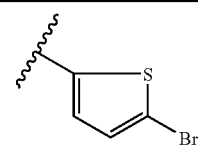 5-bromothiophen-2-yl | 2R-trans |
| 96 | B5 | cb | O=S(=O) | cb |  4,5-dichlorothiophen-2-yl | 2R-trans |
| 97 | B5 | cb | O=S(=O) | cb | 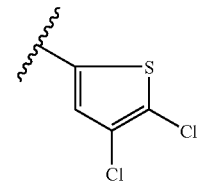 2,5-dichlorothiophen-3-yl | 2R-trans |
| 98 | B5 | cb | O=S(=O) | cb |  3-bromothiophen-5-yl with Br | 2R-trans |
| 99 | B5 | cb | O=S(=O) | cb | 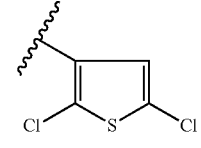 2,5-dichloro-3-bromothiophen-4-yl | 2R-trans |
| 100 | B5 | cb | O=S(=O) | cb |  1,2-dimethylimidazol-4-yl | 2R-trans |
| 101 | B5 | cb | O=S(=O) | cb | 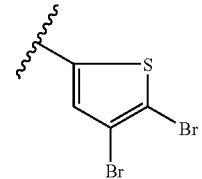 3,5-dimethylisoxazol-4-yl | 2R-trans |

TABLE 1-continued

| Comp. No. | Exp. No. | Alk$^a$ | Y | Alk$^b$ | L | stereo descriptors |
|---|---|---|---|---|---|---|
| 102 | B5 | cb | O=S=O | cb | phenyl | 2R-trans |
| 103 | B5 | cb | O=S=O | cb | 2-methylphenyl | 2R-trans |
| 104 | B5 | cb | O=S=O | cb | 3-methylphenyl | 2R-trans |
| 105 | B5 | cb | O=S=O | cb | 4-methylphenyl | 2R-trans |
| 106 | B5 | cb | O=S=O | cb | 2-chlorophenyl | 2R-trans |
| 107 | B5 | cb | O=S=O | cb | 3-chlorophenyl | 2R-trans |
| 108 | B5 | cb | O=S=O | cb | 4-chlorophenyl | 2R-trans |

TABLE 1-continued

| Comp. No. | Exp. No. | Alk$^a$ | Y | Alk$^b$ | L | stereo descriptors |
|---|---|---|---|---|---|---|
| 109 | B5 | cb | O=S=O | cb | 2,3-dichlorophenyl | 2R-trans |
| 110 | B5 | cb | O=S=O | cb | 2,5-dichlorophenyl | 2R-trans |
| 111 | B5 | cb | O=S=O | cb | 2,6-dichlorophenyl | 2R-trans |
| 112 | B5 | cb | O=S=O | cb | 2,4-dichlorophenyl | 2R-trans |
| 113 | B5 | cb | O=S=O | cb | 3,4-dichlorophenyl | 2R-trans |
| 114 | B5 | cb | O=S=O | cb | 3,5-dichlorophenyl | 2R-trans |
| 115 | B5 | cb | O=S=O | cb | 2,4,5-trichlorophenyl | 2R-trans |

TABLE 1-continued
| Comp. No. | Exp. No. | Alk^a | Y | Alk^b | L | stereo descriptors |
|---|---|---|---|---|---|---|
| 116 | B5 | cb | O=S=O | cb | 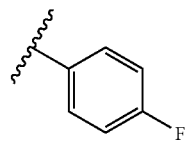 4-F-phenyl | 2R-trans |
| 117 | B5 | cb | O=S=O | cb |  4-CF₃-phenyl | 2R-trans |
| 118 | B5 | cb | O=S=O | cb | 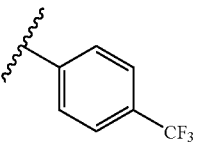 2-CN-phenyl | 2R-trans |
| 119 | B5 | cb | O=S=O | cb |  4-CN-phenyl | 2R-trans |
| 120 | B5 | cb | O=S=O | cb | 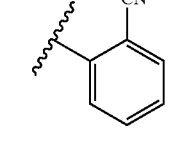 3-OMe-phenyl | 2R-trans |
| 121 | B5 | cb | O=S=O | cb |  4-OMe-phenyl | 2R-trans |
| 122 | B5 | cb | O=S=O | cb | 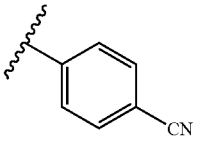 3,4-diOMe-phenyl | 2R-trans |

TABLE 1-continued

| Comp. No. | Exp. No. | Alk$^a$ | Y | Alk$^b$ | L | stereo descriptors |
|---|---|---|---|---|---|---|
| 123 | B5 | cb | O=S=O | cb | 2,5-dimethoxyphenyl | 2R-trans |
| 124 | B5 | cb | O=S=O | cb | 4-(acetylamino)phenyl | 2R-trans |
| 125 | B5 | cb | O=S=O | cb | 2-(methylsulfonyl)phenyl | 2R-trans |
| 126 | B5 | cb | O=S=O | —CH$_2$— | phenyl | 2R-trans |
| 127 | B5 | cb | O=S=O | —CH$_2$— | 3-chlorophenyl | 2R-trans |
| 128 | B5 | cb | O=S=O | —CH=CH— | phenyl | 2R-trans | cb: covalent bond

TABLE 2
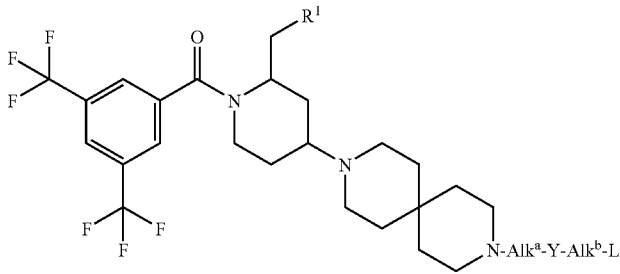
| Comp. No. | Exp. No. | R[1] | Alk[a] | Y | Alk[b] | L | Physical data |
|---|---|---|---|---|---|---|---|
| 129 | B2 | 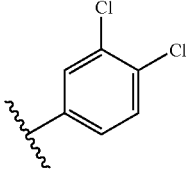 | cb | cb | cb | H | 2R-trans |
| 130 | B2 | 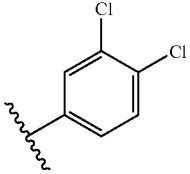 | cb | C=O | cb | 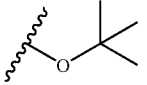 | 2R-trans |
| 131 | B2 | 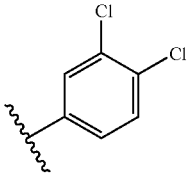 | cb | C=O | cb |  | 2R-trans |
| 132 | B2 | 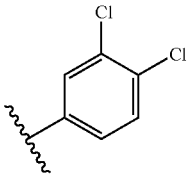 | cb | C=O | cb | 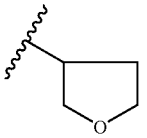 | 2R-trans |
| 133 | B2 | 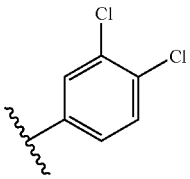 | cb | C=O | cb | 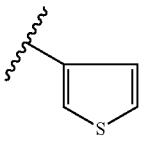 | 2R-trans |
| 134 | B2 | 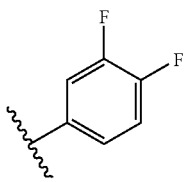 | cb | cb | cb | H | 2R-trans |

TABLE 2-continued

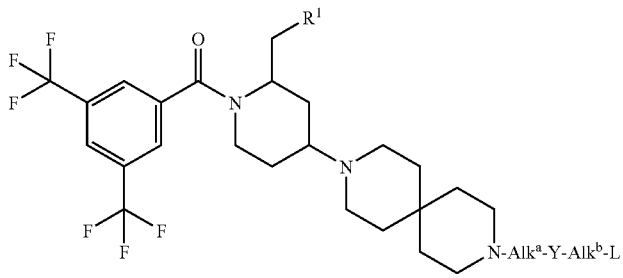

| Comp. No. | Exp. No. | R¹ | Alk$^a$ | Y | Alk$^b$ | L | Physical data |
|---|---|---|---|---|---|---|---|
| 135 | B2 | 3,4-difluorophenyl | —CH$_2$— | cb | cb | phenyl | 2R-trans |
| 136 | B2 | 3,4-difluorophenyl | cb | C=O | cb | cyclopropyl | 2R-trans |
| 137 | B2 | 3,4-difluorophenyl | cb | C=O | cb | tetrahydrofuran-3-yl | 2R-trans |
| 138 | B2 | 3,4-difluorophenyl | cb | C=O | cb | 5,5-dimethyl-2-oxotetrahydrofuran-3-yl | 2R-trans |
| 139 | B2 | 3,4-difluorophenyl | cb | C=O | cb | 5-oxopyrrolidin-2-yl | 2R-trans |
| 140 | B2 | 3,4-difluorophenyl | cb | C=O | cb | furan-3-yl | 2R-trans |

TABLE 2-continued
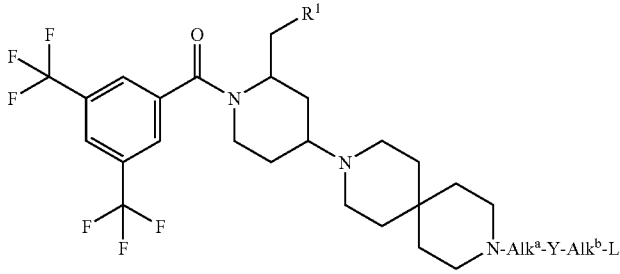
| Comp. No. | Exp. No. | R¹ | Alkᵃ | Y | Alkᵇ | L | Physical data |
|---|---|---|---|---|---|---|---|
| 141 | B2 | 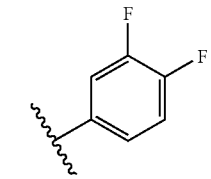 | cb | C=O | cb | 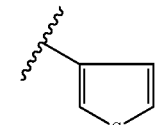 | 2R-trans |
cb: covalent bond
TABLE 3
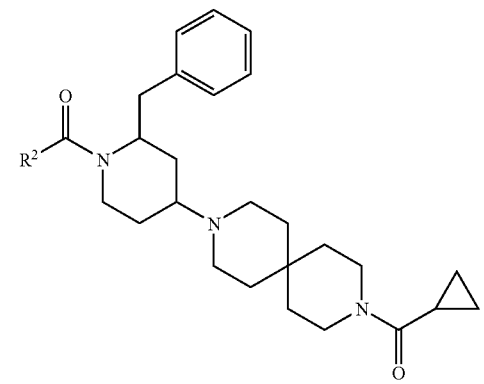
| Comp. No. | Exp. No. | R² | stereo descriptors |
|---|---|---|---|
| 143 | B3 | 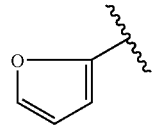 | 2R-trans |
| 144 | B3 | 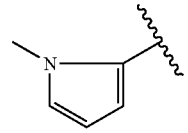 | 2R-trans |
| 145 | B3 | 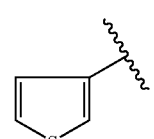 | 2R-trans |
TABLE 3-continued
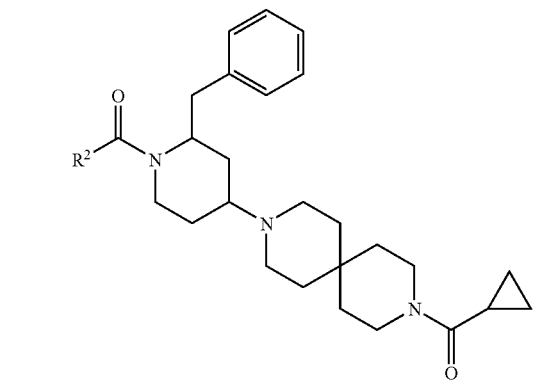
| Comp. No. | Exp. No. | R² | stereo descriptors |
|---|---|---|---|
| 162 | B3 | 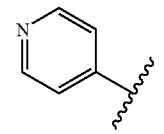 | 2R-trans |
| 163 | B3 | 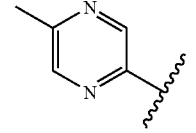 | 2R-trans |
| 146 | B3 | 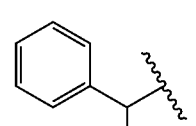 | 2R-trans |

TABLE 3-continued
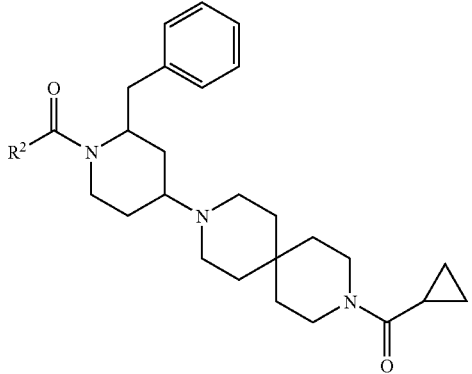
| Comp. No. | Exp. No. | R² | stereo descriptors |
|---|---|---|---|
| 147 | B3 | 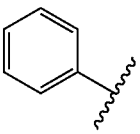 | 2R-trans |
| 148 | B3 | 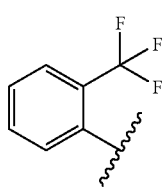 | 2R-trans |
| 149 | B3 | 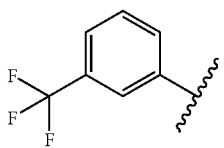 | 2R-trans |
| 150 | B3 | 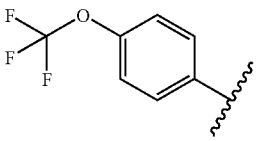 | 2R-trans |
| 151 | B3 | 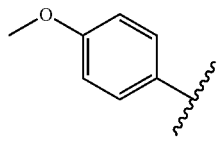 | 2R-trans |
| 152 | B3 | 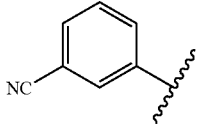 | 2R-trans |
| 153 | B3 | 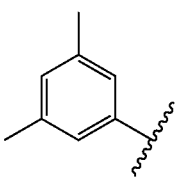 | 2R-trans |
TABLE 3-continued
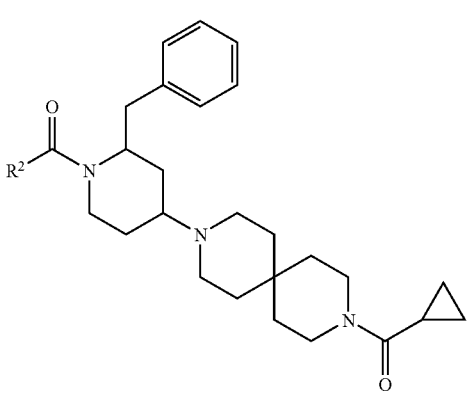
| Comp. No. | Exp. No. | R² | stereo descriptors |
|---|---|---|---|
| 154 | B3 | 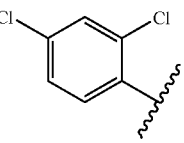 | 2R-trans |
| 155 | B3 | 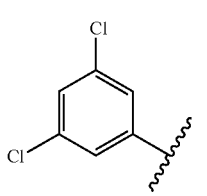 | 2R-trans |
| 156 | B3 | 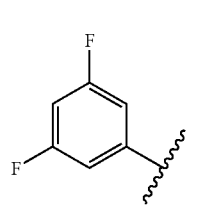 | 2R-trans |
| 157 | B3 | 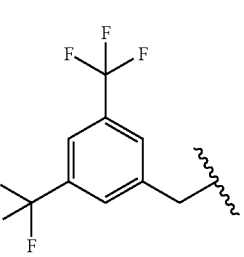 | 2R-trans |
| 158 | B3 | 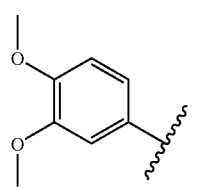 | 2R-trans |

TABLE 3-continued

| Comp. No. | Exp. No. | R² | stereo descriptors |
|---|---|---|---|
| 159 | B3 | 3,5-dimethoxyphenyl | 2R-trans |
| 160 | B3 | 3,4,5-trimethoxyphenyl | 2R-trans |
| 161 | B3 | 3,4,5-trimethoxybenzyl | 2R-trans |
| 164 | B3 | 1H-indol-5-yl | 2R-trans |
| 165 | B3 | naphthalen-2-yl | 2R-trans |
| 166 | B3 | quinolin-2-yl | 2R-trans |

TABLE 4

| Comp. No. | Exp. No. | Alkᵃ | Y | Alkᵇ | L | stereo descriptors |
|---|---|---|---|---|---|---|
| 168 | B1c | cb | cb | cb | H | 2R-trans |
| 169 | B1c | cb | cb | cb | H | 2R-cis |
| 170 | B1a | —CH₂— | cb | cb | phenyl | 2R-trans |
| 171 | B1b | —CH₂— | cb | cb | phenyl | 2R-cis |
| 172 | B2 | cb | C=O | cb | cyclopropyl | 2R-trans |
| 173 | B2 | cb | C=O | cb | cyclopropyl | 2R-cis |
| 174 | B2 | cb | C=O | cb | tetrahydrofuran-3-yl | 2R-trans |
| 175 | B2 | cb | C=O | cb | thiophen-3-yl | 2R-trans |
| 176 | B2 | cb | C=O | cb | furan-2-yl | 2R-trans | cb: covalent bond

TABLE 5
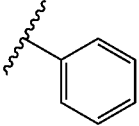
| Comp. No. | Exp. No. | Z | Alk$^a$ | Y | Alk$^b$ | L | stereo descriptors |
|---|---|---|---|---|---|---|---|
| 177 | B1.c | —CH$_2$— | cb | cb | cb | H | 2S-trans |
| 178 | B10 | —CH$_2$— | —CH$_2$— | cb | cb | 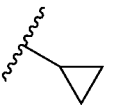 | 2S-trans |
| 179 | B2 | —CH$_2$— | cb | C=O | cb | 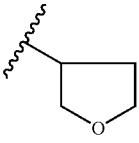 | 2S-trans |
| 180 | B2 | —CH$_2$— | cb | C=O | cb | 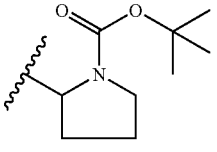 | 2S-trans |
| 181 | B2 | —CH$_2$— | cb | C=O | cb | 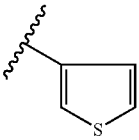 | 2S-trans |
| 182 | B2 | —CH$_2$— | cb | C=O | cb | 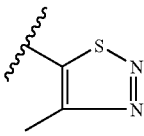 | 2S-trans |
| 183 | B2 | —CH$_2$— | cb | C=O | cb |  | 2S-trans |
| 184 | B1.c | C=O | cb | cb | cb | H | 2S-trans |

TABLE 5-continued
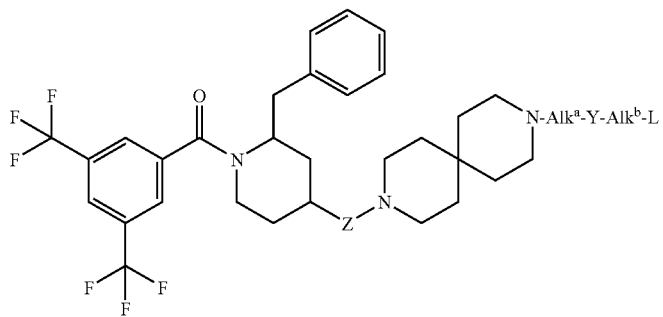
| Comp. No. | Exp. No. | Z | Alk$^a$ | Y | Alk$^b$ | L | stereo descriptors |
|---|---|---|---|---|---|---|---|
| 185 | B9 | C=O | —CH$_2$— | cb | cb | 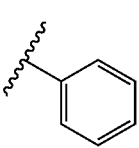 | 2S-trans |
| 186 | B2 | C=O | cb | C=O | cb | 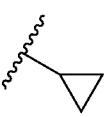 | 2S-trans |
| 187 | B2 | C=O | cb | C=O | cb | 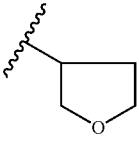 | 2S-trans |
| 188 | B2 | C=O | cb | CO | cb | 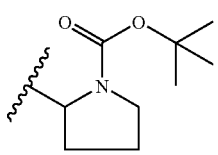 | 2S-trans |
| 189 | B2 | C=O | cb | C=O | cb | 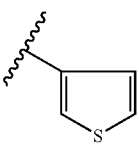 | 2S-trans |
| 190 | B2 | C=O | cb | C=O | cb | 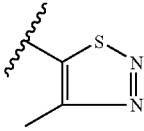 | 2S-trans |
cb: covalent bond

TABLE 6

| Comp. No. | Exp. No. | Alk$^a$ | Y | Alk$^b$ | L | stereo descriptors |
|---|---|---|---|---|---|---|
| 191 | B8.a | cb | cb | cb | H | 2R-trans |
| 192 | B8.a | cb | cb | cb | H | 2R-cis |
| 193 | B9 | —CH$_2$— | cb | cb | isopropyl | 2R-cis |
| 194 | B9 | —CH$_2$— | cb | cb | 3-pentyl | 2R-cis |
| 195 | B8.b | —CH$_2$— | cb | cb | cyclopropyl | 2R-trans |
| 196 | B8.b | —CH$_2$— | cb | cb | cyclopropyl | 2R-cis |
| 197 | B9 | —CH$_2$— | cb | cb | cyclobutyl | 2R-cis |
| 198 | B8.b | —CH$_2$— | cb | cb | furan-3-yl | 2R-cis |
| 199 | B8.b | —CH$_2$— | cb | cb | furan-3-yl | 2R-trans |
| 200 | B9 | —CH$_2$— | cb | cb | 3,5-dimethylisoxazol-4-yl | 2R-trans |
| 201 | B9 | —CH$_2$— | cb | cb | 3,5-dimethylisoxazol-4-yl | 2R-cis |
| 202 | B9 | —CH$_2$— | cb | cb | 2-fluorophenyl | 2R-trans |
| 203 | B9 | —CH$_2$— | cb | cb | 2-fluorophenyl | 2R-cis |
| 204 | B9 | —CH$_2$— | C=O | cb | adamantyl | 2R-trans |
| 205 | B9 | —CH$_2$— | C=O | cb | adamantyl | 2R-cis | cb: covalent bond

TABLE 7

[Structure: 3,5-bis(trifluoromethyl)benzoyl group attached to N of a 2-benzyl-piperidine, with 4-position connected to a 2,8-diazaspiro[5.5]undecane bearing N-Alk$^a$-Y-Alk$^b$-L]

| Comp. No. | Exp. No. | Alk$^a$ | Y | Alk$^b$ | L | stereo descriptors |
|---|---|---|---|---|---|---|
| 206 | B10 | cb | cb | cb | H | 2R-trans |
| 207 | B11 | cb | C=O | cb | *tert*-butyl | 2R-trans |
| 208 | B11 | cb | C=O | cb | cyclopropyl | 2R-trans |
| 209 | B11 | cb | C=O | cb | -O-*tert*-butyl | 2R-trans |
| 210 | B11 | cb | C=O | cb | tetrahydrofuran-3-yl | 2R-trans |
| 211 | B11 | cb | C=O | cb | tetrahydrofuran-3-yl | 2R-cis |
| 212 | B11 | cb | C=O | cb | furan-3-yl | 2R-trans |
| 213 | B11 | cb | C=O | cb | furan-3-yl | 2R-cis |
| 214 | B11 | cb | C=O | cb | thiophen-3-yl | 2R-trans |
| 215 | B11 | cb | C=O | cb | phenyl | 2R-trans | cb: covalent: bond

C. Analytical Data

For a number of compounds, either melting points or LCMS data were recorded.

1. Melting Points

If possible, melting points (or ranges) were obtained with a Leica VMHB Koffler bank. The melting points are uncorrected.

TABLE 8

Melting points for selected compounds.

| Compound no. | Result (° C.) |
|---|---|
| 3 | 143 |
| 5 | 183 |
| 21 | 110 |
| 24 | 132 |
| 36 | 125 |
| 42 | 162 |
| 92 | 132 |
| 130 | 80 |
| 131 | 90 |
| 132 | 110 |
| 133 | 109 |
| 136 | 160 |
| 137 | 100 |
| 140 | 92 |
| 141 | 96 |
| 172 | 122 |
| 173 | 128 |
| 174 | 130 |
| 175 | 124 |
| 185 | 90 |
| 178 | 220 |

2. LCMS Conditions

The HPLC gradient was supplied by a Waters Alliance HT 2795 system (Waters, Milford, Mass.) at room temperature. Flow from the column was split to a Waters 996 photodiode array (PDA) detector and a Waters-LCT mass spectrometer with an electrospray ionization source operated in positive ionization mode. Reversed phase HPLC was carried out on a Kromasil C18 column (5 µm, 4.6×150 mm) with a flow rate of 1 ml/min. Two mobile phases (mobile phase A: 100% 6.5 mM ammonium acetate+0.2% formic acid; mobile phase B: 100% acetonitrile) were employed to run a gradient condition from 60% A & 40% B for 1 min to 100% B in 4 min., 100% B for 5 min to 60% A & 40% B in 3 min, and re-equilibrate with 60% A & 40% B for 3 min).

Mass spectra were acquired by scanning from 100 to 900 in 1 s using a dwell time of 0.1 s. The capillary needle voltage was 3 kV and the source temperature was maintained at 100° C. Nitrogen was used as the nebulizer gas. Cone voltage was 20 V for positive ionization mode. Data acquisition was performed with a Waters-Micromass MassLynx-Openlynx data system.

TABLE 9

LCMS parent peak and retention time for selected compounds.

| Comp. no. | LCMS MS(MH+) | Retention time (min) |
|---|---|---|
| 3 | 636 | 9.0 |
| 4 | 679 | 3.8 |
| 5 | 658 | 3.4 |
| 6 | 694 | 2.9 |
| 7 | 652 | 4.9 |
| 8 | 652 | 5.0 |
| 9 | 664 | 4.9 |
| 10 | 636 | 4.6 |
| 11 | 650 | 4.51 |
| 12 | 704 | 4.73 |
| 13 | 661 | 4.47 |
| 14 | 679 | 3.97 |
| 15 | 650 | 4.6 |
| 16 | 692 | 5.4 |
| 17 | 664 | 5.1 |
| 18 | 664 | 5.0 |
| 19 | 690 | 5.0 |
| 20 | 666 | 4.3 |
| 21 | 666 | 4.2 |
| 22 | 679 | 4.0 |
| 23 | 662 | 4.6 |
| 24 | 662 | 4.7 |
| 25 | 676 | 4.8 |
| 26 | 676 | 4.7 |
| 27 | 676 | 4.7 |
| 28 | 678 | 4.7 |
| 29 | 692 | 5.1 |
| 30 | 692 | 5.3 |
| 31 | 692 | 5.0 |
| 32 | 692 | 4.9 |
| 33 | 675 | 4.6 |
| 34 | 676 | 3.9 |
| 35 | 691 | 4.5 |
| 36 | 694 | 4.8 |
| 37 | 692 | 5.4 |
| 38 | 692 | 5.3 |
| 39 | 692 | 5.3 |
| 40 | 734 | 14.3 |
| 41 | 676 | 4.8 |
| 42 | 706 | 4.9 |
| 43 | 697 | 4.7 |
| 44 | 737 | 5.2 |
| 45 | 678 | 4.5 |
| 46 | 690 | 4.3 |
| 47 | 718 | 4.4 |
| 48 | 691 | 8.2 |
| 49 | 673 | 4.3 |
| 50 | 673 | 4.2 |
| 51 | 673 | 4.1 |
| 52 | 674 | 4.2 |
| 53 | 689 | 4.2 |
| 54 | 689 | 3.9 |
| 55 | 689 | 3.8 |
| 57 | 689 | 4.0 |
| 58 | 692 | 4.1 |
| 59 | 730 | 5.9 |
| 60 | 730 | 5.8 |
| 61 | 748 | 5.3 |
| 62 | 716 | 4.8 |
| 63 | 716 | 5.1 |

TABLE 9-continued

LCMS parent peak and retention time for selected compounds.

| Comp. no. | LCMS MS(MH+) | Retention time (min) |
|---|---|---|
| 64 | 712 | 5.5 |
| 65 | 724 | 4.8 |
| 66 | 724 | 4.8 |
| 67 | 726 | 3.2 |
| 68 | 714 | 5.0 |
| 69 | 666 | 5.0 |
| 70 | 676 | 5.0 |
| 71 | 692 | 5.2 |
| 72 | 744 | 6.0 |
| 73 | 719 | 4.4 |
| 74 | 730 | 5.6 |
| 75 | 692 | 4.8 |
| 76 | 692 | 4.8 |
| 77 | 678 | 4.2 |
| 78 | 693 | 3.9 |
| 79 | 695 | 4.1 |
| 80 | 734 | 4.1 |
| 81 | 730 | 5.1 |
| 82 | 742 | 4.8 |
| 83 | 730 | 5.2 |
| 84 | 688 | 5.2 |
| 85 | 688 | 4.9 |
| 86 | 704 | 5.1 |
| 87 | 712 | 5.2 |
| 88 | 716 | 4.6 |
| 89 | 712 | 5.0 |
| 90 | 740 | 5.6 |
| 91 | 700 | 5.3 |
| 92 | 714 | 5.0 |
| 93 | 714 | 5.1 |
| 94 | 748 | 5.5 |
| 95 | 792 | 5.7 |
| 96 | 782 | 6.0 |
| 97 | 782 | 5.8 |
| 98 | 870 | 6.0 |
| 99 | 860 | 6.0 |
| 100 | 726 | 4.4 |
| 101 | 727 | 5.2 |
| 102 | 708 | 5.2 |
| 103 | 722 | 5.4 |
| 104 | 722 | 5.4 |
| 105 | 722 | 5.4 |
| 106 | 742 | 5.4 |
| 107 | 742 | 5.5 |
| 108 | 742 | 5.5 |
| 109 | 776 | 5.6 |
| 110 | 776 | 5.7 |
| 111 | 776 | 5.5 |
| 112 | 776 | 5.8 |
| 113 | 776 | 5.8 |
| 114 | 776 | 5.8 |
| 115 | 810 | 6.1 |
| 116 | 726 | 5.3 |
| 117 | 776 | 5.7 |
| 118 | 733 | 5.1 |
| 119 | 733 | 5.2 |
| 120 | 738 | 5.2 |
| 121 | 738 | 5.3 |
| 122 | 768 | 5.0 |
| 123 | 768 | 5.2 |
| 124 | 765 | 4.8 |
| 125 | 786 | <5 |
| 126 | 722 | 5.2 |
| 127 | 756 | 5.4 |
| 128 | 734 | 5.4 |
| 130 | 736 | 5.7 |
| 131 | 704 | 5.0 |
| 132 | 734 | 4.8 |
| 133 | 746 | 5.2 |
| 134 | 604.0 | 12.8 |
| 136 | 672 | 4.6 |
| 137 | 702 | 4.4 |
| 138 | 744 | 4.5 |
| 139 | 715 | 3.9 |

TABLE 9-continued

LCMS parent peak and retention time for selected compounds.

| Comp. no. | LCMS MS(MH+) | Retention time (min) |
|---|---|---|
| 140 | 698 | 4.7 |
| 141 | 714 | 4.8 |
| 143 | 490 | 3.7 |
| 144 | 503 | 2.4 |
| 145 | 506 | 2.2 |
| 146 | 528 | 3.7 |
| 147 | 500 | 2.5 |
| 148 | 568 | 8.2 |
| 149 | 568 | 3.8 |
| 150 | 584 | 4.0 |
| 151 | 530 | 2.6 |
| 152 | 525 | 2.3 |
| 153 | 528 | 3.7 |
| 154 | 568 | 3.8 |
| 155 | 568 | 8.7 |
| 156 | 536 | 3.3 |
| 157 | 650 | 4.8 |
| 158 | 560 | 4.0 |
| 159 | 560 | 2.9 |
| 160 | 590 | 2.2 |
| 161 | 604 | 2.4 |
| 162 | 501 | 6.7 |
| 163 | 516 | 6.7 |
| 164 | 539 | 2.3 |
| 165 | 550 | 3.8 |
| 166 | 551 | 2.9 |
| 167 | 674 | 4.9 |
| 170 | 658 | 6.1 |
| 172 | 636 | 4.7 |
| 173 | 636 | 4.8 |
| 174 | 666 | 4.4 |
| 175 | 678 | 4.9 |
| 176 | 662 | 4.8 |
| 178 | 686 | 4.9 |
| 178 | 672 | 3.4 |
| 179 | 650 | 4.6 |
| 180 | 680 | 4.3 |
| 181 | 779 | <5 |
| 182 | 692 | 4.8 |
| 183 | 708 | 4.7 |
| 186 | 664 | 6.3 |
| 187 | 694 | 5.9 |
| 188 | 793 | 6.6 |
| 189 | 706 | 6.4 |
| 190 | 722 | 6.3 |
| 192 | 582 | 3.94 |
| 193 | 638 | 4.76 |
| 194 | 666 | 5.23 |
| 195 | 636 | 4.63 |
| 196 | 636 | 4.63 |
| 197 | 650 | 4.83 |
| 198 | 662 | 4.71 |
| 199 | 662 | 4.6 |
| 200 | 691 | 4.44 |
| 201 | 691 | 4.54 |
| 202 | 690 | 4.9 |
| 203 | 690 | 5.03 |
| 204 | 758 | 5.7 |
| 205 | 758 | 5.87 |
| 207 | 652 | 5.53 |
| 208 | 636 | 4.94 |
| 210 | 666 | 4.63 |
| 211 | 666 | 4.74 |
| 212 | 662 | <5 |
| 213 | 662 | 5.1 |
| 214 | 678 | 5.24 |
| 215 | 672 | 5.3 |

D. Pharmacological Example

EXAMPLE D.1

Binding Experiment for h-$NK_1$, h-$NK_2$ and h-$NK_3$ Receptors

The compounds according to the invention were investigated for interaction with various neurotransmitter receptors, ion channels and transporter binding sites using the radioligand binding technique. Membranes from tissue homogenates or from cells, expressing the receptor or transporter of interests, were incubated with a radioactively labelled substance ([$^3$H]—or [$^{125}$I] ligand) to label a particular receptor. Specific receptor binding of the radioligand was distinguished from the non-specific membrane labelling by selectively inhibiting the receptor labelling with an unlabelled drug (the blank), known to compete with the radioligand for binding to the receptor sites. Following incubation, labelled membranes were harvested and rinsed with excessive cold buffer to remove non-bound radioactivity by rapid filtration under suction. Membrane bound radioactivity was counted in a scintillation counter and results were expressed in counts per minute (cpm).

The compounds were dissolved in DMSO and tested at 10 concentrations ranging from $10^{-10}$ to $10^{-5}$ M.

The ability of the compounds according to the invention to displace [$^3$H]-Substance P from cloned human h-$NK_1$ receptors expressed in CHO cells, to displace [$^3$H]—SR-48968 from cloned human h-$NK_2$ receptors expressed in Sf9 cells, and to displace [$^3$H]—SR-142801 from cloned human h-$NK_3$ receptors expressed in CHO cells was evaluated.

The receptor binding values (p$IC_{50}$) for the h-$NK_1$ ranges for all compounds according to the invention between 10 and 6.

EXAMPLE D.2

Signal Transduction (ST)

This test evaluates in vitro functional $NK_1$ antagonistic activity. For the measurements of intracellular $Ca^{++}$ concentrations the cells were grown on 96-well (black wall/transparent bottom) plates from Costar for 2 days until they reached confluence. The cells were loaded with 2 μM Fluo3 in DMEM containing 0.1% BSA and 2.5 mM probenecid for 1 h at 37° C. They were washed 3× with a Krebs buffer (140 mM NaCl, 1 mM $MgCl_2 \times 6H_2O$, 5 mM KCl, 10 mM glucose, 5 mM HEPES; 1.25 mM $CaCl_2$; pH 7.4) containing 2.5 mM probenecid and 0.1% BSA ($Ca^{++}$-buffer). The cells were pre-incubated with a concentration range of antagonists for 20 min at RT and $Ca^{++}$-signals after addition of the agonists were measured in a Fluorescence Image Plate Reader (FLIPR from Molecular Devices, Crawley, England). The peak of the $Ca^{++}$-transient was considered as the relevant signal and the mean values of corresponding wells were analysed as described below.

The sigmoidal dose response curves were analysed by computerised curve-fitting, using the GraphPad Program. The $EC_{50}$-value of a compound is the effective dose showing 50% of maximal effect. For mean curves the response to the agonist with the highest potency was normalised to 100%. For antagonist responses the $IC_{50}$-value was calculated using non-linear regression.

The p$IC_{50}$ data for the signal transduction testing for a representative selection of compounds are presented in Table 10. The last columns indicate—without being limited thereto—for which action the compounds might be most suitable. Of course, since for some neurokinin receptors no data was determined, it is obvious that these compounds might be attributed to another suitable use.

TABLE 10

Pharmacological data for the signal transduction for selected compounds.

| Comp. No | $NK_1$ $pIC_{50}$ | NK2 pIC50 | NK3 pIC50 | Suitable for |
|---|---|---|---|---|
| 98 | 6.01 | <5 | <5 | NK1 |
| 40 | 6.01 | <5 | <5 | NK1 |
| 64 | 6.05 | <5 | <5 | NK1 |
| 30 | 6.16 | 5.1 | <5 | NK1 |
| 203 | 6.18 | 5.47 | <5 | NK1 |
| 212 | 6.20 | 5.45 | 5.42 | NK1 |
| 207 | 6.23 | 5.72 | 5.24 | NK1 |
| 99 | 6.25 | <5 | <5 | NK1 |
| 128 | 6.25 | 5.27 | <5 | NK1 |
| 112 | 6.26 | <5 | <5 | NK1 |
| 201 | 6.66 | 5.55 | ~5 | NK1 |
| 115 | 6.31 | <5 | <5 | NK1 |
| 96 | 6.33 | 5.9 | ~5 | NK1 |
| 117 | 6.35 | <5 | <5 | NK1 |
| 63 | 6.36 | 5.1 | <5 | NK1 |
| 63 | 6.36 | 5.1 | <5 | NK1 |
| 178 | 6.36 | 5.31 | <5 | NK1 |
| 113 | 6.37 | <5 | <5 | NK1 |
| 74 | 6.41 | <5 | <5 | NK1 |
| 87 | 6.41 | 5.22 | <5 | NK1 |
| 114 | 6.44 | <5 | <5 | NK1 |
| 90 | 6.45 | 5.27 | <5 | NK1 |
| 59 | 6.46 | <5 | 5.23 | NK1 |
| 208 | 6.46 | 5.58 | 5.37 | NK1 |
| 198 | 6.47 | 5.32 | <5 | NK1 |
| 72 | 6.49 | <5 | <5 | NK1 |
| 108 | 6.49 | 5.58 | 5.4 | NK1 |
| 85 | 6.51 | <5 | <5 | NK1 |
| 68 | 6.53 | 5.25 | <5 | NK1 |
| 84 | 6.55 | 5.14 | <5 | NK1 |
| 211 | 6.55 | 5.34 | ~5 | NK1 |
| 78 | 6.57 | <5 | <5 | NK1 |
| 95 | 6.57 | 5.72 | 5.63 | NK1 |
| 61 | 6.58 | <5 | <5 | NK1 |
| 127 | 6.58 | 5.33 | <5 | NK1 |
| 202 | 6.61 | 5.34 | 5.14 | NK1 |
| 60 | 6.62 | 5.33 | 5.33 | NK1 |
| 193 | 6.62 | 5.6 | 5.24 | NK1 |
| 48 | 6.66 | <5 | <5 | NK1 |
| 196 | 6.67 | 5.19 | ~5.51 | NK1 |
| 33 | 6.70 | <5 | <5 | NK1 |
| 16 | 6.72 | <5 | 5.07 | NK1 |
| 34 | 6.72 | 5.21 | <5 | NK1 |
| 197 | 6.72 | 5.54 | 5.19 | NK1 |
| 62 | 6.73 | <5 | <5 | NK1 |
| 110 | 6.76 | n.d. | 5.29 | NK1 |
| 79 | 6.77 | <5 | <5 | NK1 |
| 44 | 6.79 | 5.35 | 5.34 | NK1 |
| 155 | 6.80 | 5.19 | n.d. | NK1 |
| 125 | 6.80 | 5.29 | 5.16 | NK1 |
| 55 | 6.80 | 5.4 | <5 | NK1 |
| 57 | 6.82 | 5.72 | <5 | NK1 |
| 41 | 6.83 | 5.07 | <5 | NK1 |
| 41 | 6.83 | 5.07 | <5 | NK1 |
| 89 | 6.83 | 5.6 | <5 | NK1 |
| 153 | 6.84 | <5 | n.d. | NK1 |
| 53 | 6.86 | <5 | <5 | NK1 |
| 86 | 6.89 | <5 | <5 | NK1 |
| 6 | 6.89 | 5.11 | <5 | NK1 |
| 15 | 6.89 | 5.5 | 5.10 | NK1 |
| 7 | 6.94 | <5 | <5 | NK1 |
| 81 | 6.94 | 5.28 | <5 | NK1 |
| 107 | 6.94 | 5.38 | 5.50 | NK1 |
| 9 | 6.97 | <5 | <5 | NK1 |
| 49 | 6.97 | 5.40 | <5 | NK1 |
| 46 | 6.98 | 5.20 | <5 | NK1 |
| 11 | 6.98 | 5.27 | n.d. | NK1 |
| 43 | 6.98 | 5.44 | <5 | NK1 |
| 37 | 7.02 | 5.09 | <5 | NK1 |
| 37 | 7.02 | 5.09 | <5 | NK1 |
| 71 | 7.03 | 5.01 | <5 | NK1 |
| 71 | 7.03 | 5.01 | <5 | NK1 |
| 172 | 7.03 | 5.16 | 5.24 | NK1 |
| 91 | 7.06 | 5.86 | 5.36 | NK1 |
| 97 | 7.06 | n.d. | ~5 | NK1 |
| 39 | 7.07 | 5.32 | 5.27 | NK1 |
| 25 | 7.08 | 5.40 | <5 | NK1 |
| 185 | 7.09 | 5.26 | <5 | NK1 |
| 70 | 7.09 | 5.27 | <5 | NK1 |
| 45 | 7.10 | 5.27 | <5 | NK1 |
| 50 | 7.11 | 5.58 | <5 | NK1 |
| 32 | 7.12 | 5.50 | 5.18 | NK1 |
| 176 | 7.14 | ~5.19 | <5 | NK1 |
| 123 | 7.15 | ~5.39 | <5 | NK1 |
| 47 | 7.18 | ~5 | <5 | NK1 |
| 66 | 7.18 | 5.43 | 5.16 | NK1 |
| 58 | 7.19 | <5 | <5 | NK1 |
| 69 | 7.19 | 5.51 | 5.18 | NK1 |
| 42 | 7.21 | 5.05 | 5.03 | NK1 |
| 42 | 7.21 | 5.05 | 5.03 | NK1 |
| 52 | 7.22 | 5.54 | <5 | NK1 |
| 179 | 7.23 | <5 | <5 | NK1 |
| 67 | 7.24 | 5.01 | <5 | NK1 |
| 67 | 7.24 | 5.01 | <5 | NK1 |
| 133 | 7.27 | 5.43 | 5.31 | NK1 |
| 101 | 7.31 | 5.70 | 5.22 | NK1 |
| 82 | 7.33 | 5.70 | 5.05 | NK1 |
| 77 | 7.34 | ~5.09 | <5 | NK1 |
| 77 | 7.34 | ~5.09 | <5 | NK1 |
| 122 | 7.35 | 5.40 | <5 | NK1 |
| 8 | 7.36 | 5.55 | 5.35 | NK1 |
| 141 | 7.38 | 5.23 | 5.15 | NK1 |
| 88 | 7.38 | 5.52 | <5 | NK1 |
| 174 | 7.39 | 5.16 | <5 | NK1 |
| 182 | 7.42 | <5 | 5.04 | NK1 |
| 182 | 7.42 | <5 | 5.04 | NK1 |
| 182 | 7.42 | <5 | 5.04 | NK1 |
| 83 | 7.44 | 5.59 | 5.05 | NK1 |
| 22 | 7.44 | 5.75 | <5 | NK1 |
| 181 | 7.47 | 5.15 | <5 | NK1 |
| 73 | 7.48 | <5 | <5 | NK1 |
| 73 | 7.48 | <5 | <5 | NK1 |
| 73 | 7.48 | <5 | <5 | NK1 |
| 126 | 7.48 | 5.47 | 5.4 | NK1 |
| 14 | 7.50 | <5 | n.d. | NK1 |
| 14 | 7.50 | <5 | n.d. | NK1 |
| 14 | 7.50 | <5 | n.d. | NK1 |
| 173 | 7.51 | ~5.79 | <5 | NK1 |
| 80 | 7.53 | <5 | <5 | NK1 |
| 80 | 7.53 | <5 | <5 | NK1 |
| 51 | 7.53 | 5.44 | <5 | NK1 |
| 189 | 7.54 | 5.17 | <5 | NK1 |
| 36 | 7.55 | 5.37 | <5 | NK1 |
| 140 | 7.63 | 5.46 | 5.61 | NK1 |
| 27 | 7.69 | 5.35 | 5.48 | NK1 |
| 187 | 7.7 | 5.15 | <5 | NK1 |
| 35 | 7.72 | <5 | <5 | NK1 |
| 35 | 7.72 | <5 | <5 | NK1 |
| 138 | 7.75 | 5.33 | <5 | NK1 |
| 183 | 7.77 | 5.11 | 5.13 | NK1 |
| 186 | 7.77 | 5.30 | 5.27 | NK1 |
| 21 | 7.78 | 5.63 | 5.67 | NK1 |
| 175 | 7.81 | 5.35 | <5 | NK1 |
| 188 | 7.82 | 5.26 | 5.43 | NK1 |
| 180 | 7.83 | 5.08 | <5 | NK1 |
| 111 | 6.69 | ~6.64 | 5.27 | NK1-2 |
| 121 | 6.95 | 5.92 | 5.43 | NK1-2 |
| 76 | 7.59 | 5.94 | 5.40 | NK1-2 |
| 200 | 7.63 | 5.84 | 5.16 | NK1-2 |
| 18 | 7.69 | 5.92 | 5.33 | NK1-2 |
| 190 | 8.21 | 5.79 | 5.45 | NK1-2 |
| 210 | 6.54 | 5.74 | 5.75 | NK1-3 |
| 94 | 6.88 | <5 | 6.24 | NK1-3 |

TABLE 10-continued

Pharmacological data for the signal transduction for selected compounds.

| Comp. No | NK$_1$ pIC$_{50}$ | NK2 pIC50 | NK3 pIC50 | Suitable for |
|---|---|---|---|---|
| 24 | 6.95 | <5 | 5.88 | NK1-3 |
| 105 | 6.98 | 5.61 | 5.70 | NK1-3 |
| 104 | 7.19 | ~5.34 | 5.71 | NK1-3 |
| 102 | 7.21 | <5 | 6.15 | NK1-3 |
| 106 | 7.22 | 5 | 6.28 | NK1-3 |
| 167 | 7.25 | 5.69 | 5.71 | NK1-3 |
| 116 | 7.28 | <5 | 6.15 | NK1-3 |
| 103 | 7.30 | 5.60 | 5.82 | NK1-3 |
| 139 | 7.41 | 5.62 | 6.02 | NK1-3 |
| 199 | 7.43 | 5.56 | 6.07 | NK1-3 |
| 118 | 7.51 | n.d. | 5.82 | NK1-3 |
| 137 | 7.56 | 5.46 | 5.77 | NK1-3 |
| 124 | 7.63 | ~5.59 | 5.75 | NK1-3 |
| 136 | 7.77 | 5.70 | 6.16 | NK1-3 |
| 119 | 7.18 | 5.97 | 5.8 | NK1-2-3 |
| 195 | 7.27 | ~5.85 | 5.84 | NK1-2-3 |
| 4 | 7.41 | 5.81 | 5.89 | NK1-2-3 |
| 3 | 7.43 | 5.96 | 5.82 | NK1-2-3 |
| 93 | 7.59 | 5.96 | 6.30 | NK1-2-3 |
| 131 | 7.76 | 6.11 | 5.85 | NK1-2-3 |
| 92 | 7.77 | 5.88 | 6.47 | NK1-2-3 |
| 100 | 7.92 | 5.9 | 6.48 | NK1-2-3 |
| 132 | 8.02 | 5.77 | 6.04 | NK1-2-3 |

(n.d. = not determined)

E. Composition Examples

"Active ingredient" (A.I.) as used throughout these examples relates to a compound of Formula (I), the pharmaceutically acceptable acid or base addition salts thereof, the stereochemically isomeric forms thereof, the N-oxide form thereof and prodrugs thereof.

EXAMPLE E.1

Oral Drops

500 Grams of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE E.2

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE E.3

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10,000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated color suspension and the whole was homogenated. The tablet cores were coated with the thus obtained in a coating apparatus.

EXAMPLE E.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

The invention claimed is:

1. A compound according to the general Formula (I)

$$Q\underset{R^2-X}{\overset{R^1}{\diagdown}}N-(CH_2)_m\underset{(CH_2)_n}{\diagdown}Z-N\underset{(CH_2)_k}{\overset{(CH_2)_j}{\diagdown}}\underset{(CH_2)_q}{\overset{(CH_2)_p}{\diagdown}}(T)_t\ N-Alk-Y-Alk-L$$

(I)

the pharmaceutically acceptable acid or base addition salts thereof, the stereochemically isomeric forms thereof, or the N-oxide form thereof, wherein:

$R^2$ is $Ar^2$, $Ar^2$-alkyl, di($Ar^2$)alkyl, $Het^1$ or $Het^1$-alkyl;

X is a covalent bond (cb) or a bivalent radical of formula —O—, —S— or —$NR^3$—;

Q is O or $NR^3$;

each $R^3$ independently from each other, is hydrogen or alkyl;

$R^1$ is selected from the group of $Ar^1$, $Ar^1$-alkyl and di($Ar^1$)-alkyl;

n is 1;

m is 1;

Z is a covalent bond or a bivalent radical of formula —CH$_2$— or >C(=O);

j, k, p, q are each 2;

T is =O in an alpha-position relative to the N-atom and t is an integer, equal to 0 or 1;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more, phenyl, halo, cyano, hydroxy, formyl and amino radicals;

Y is a covalent bond or a bivalent radical of formula —C(=O)—, —SO$_2$—>C=CH—R or >C=N—R, wherein R is H, CN or nitro;

L is selected from the group of hydrogen, alkyl, alkenyl, alkyloxy, alkyloxyalkyloxy, alkylcarbonyloxy, alkyloxycarbonyl, mono- and di(alkyl)amino, mono- and di(alkyloxycarbonyl)amino, mono- and di(alkylcarbonyl)amino, mono-and di(Ar$^3$)amino, mono-and di(Ar$^3$alkyl)-amino, mono-and di(Het$^2$)amino, mono- and di(Het$^2$alkyl)amino, alkylsulfanyl, norbornyl, adamantyl, tricycloundecyl, Ar$^3$, Ar$^3$-oxy, Ar$^3$carbonyl, Het$^2$, Het$^2$ carbonyl and mono- and di(Het$^2$carbonyl) amino;

Ar$^1$ is phenyl, optionally substituted with 1, 2 or 3 substituents, each independently from each other, selected from the group of halo, alkyl, cyano, aminocarbonyl and alkyloxy;

Ar$^2$ is naphthalenyl or phenyl, each optionally substituted with 1, 2 or 3 substituents, each independently from each other, selected from the group of halo, nitro, amino, mono- and di(alkyl)amino, cyano, alkyl, hydroxy, alkyloxy, carboxyl, alkyloxycarbonyl, aminocarbonyl and mono- and di(alkyl)aminocarbonyl;

Ar$^3$ is naphthalenyl or phenyl, optionally substituted with 1, 2 or 3 substituents, each independently from each other, selected from the group of alkyloxy, alkylcarbonylamino, methanesulfonyl, Ar$^1$carbonyloxyalkyl, Ar$^1$alkyloxycarbonyl, Ar$^1$alkyloxyalkyl, alkyl, halo, hydroxy, pyridinyl, morpholinyl, pyrrolyl, pyrrolidinyl, imidazo [1,2-a]pyridinyl, morpholinylcarbonyl, pyrrolidinylcarbonyl, amino and cyano;

Het$^1$ is a monocyclic heterocyclic radical selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl, benzothienyl, indanyl and chromenyl; wherein each mono- and bicyclic heterocyclic radical may optionally be substituted on any atom by one or more radicals, each independently from each other, selected from the group of halo, oxo and alkyl;

Het$^2$ is a monocyclic heterocyclic radical selected from the group of pyrrolidinyl, dihydro-2H-pyranyl, pyranyl, dioxolyl, tetrahydropyridinyl, tetrahydropyrimidinyl, pyrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrazolinyl, pyrrolyl, imidazolyl, pyrazolyl, triazolyl, furanyl, thienyl, oxazolyl, dioxazolyl, oxazolinyl, isoxazolyl, thiazolyl, thiadiazolyl, isothiazolyl, pyridinyl, 1H-pyridinyl, pyrimidinyl, pyrazinyl, pyridazinyl, triazinyl and tetrazolyl; or a bicyclic heterocyclic radical selected from the group of 2,3-dihydro-benzo[1,4]dioxine, octahydro-benzo[1,4]dioxine, octabicycloheptyl, benzopiperidinyl, quinolinyl, quinoxalinyl, indolyl, isoindolyl, chromanyl, benzimidazolyl, imidazo[1,2-a]pyridinyl, benzoxazolyl, benzodioxolyl, benzisoxazolyl, benzoxadiazolyl, benzothiazolyl, benzisothiazolyl, benzofuranyl, dihydroisobenzofuranyl, or benzothienyl; wherein each mono-, and bicyclic heterocyclic radical may optionally be substituted on any atom with one or more radicals selected from the group of Ar$^1$, Ar$^1$alkyl, Ar$^1$alkyloxyalkyl, halo, hydroxy, alkyl, piperidinyl, pyrrolyl, thienyl, oxo, alkyloxy, alkylcarbonyl, Ar$^1$ carbonyl, mono- and di(alkyl)aminoalkyl, alkyloxyalkyl and alkyloxycarbonyl;

alkyl is a straight or branched saturated hydrocarbon radical having from 1 to 6 carbon atoms or a cyclic saturated hydrocarbon radicals having from 3 to 6 carbon atoms; each hydrocarbon radical optionally substituted on one or more carbon atoms with one or more radicals selected from the group of phenyl, halo, trihalomethyl, aminocarbonyl, methyl, ethyl, propyl, isopropyl, t-butyl, cyano, oxo, hydroxy, formyl and amino; and alkenyl is a straight or branched unsaturated hydrocarbon radical having from 1 to 6 carbon atoms and having 1 or more unsaturated bonds; or a cyclic unsaturated hydrocarbon radical having from 3 to 6 carbon atoms and having 1 or more unsaturated bonds; each hydrocarbon radical optionally substituted on one or more carbon atoms with one or more radicals selected from the group of phenyl, halo, cyano, oxo, hydroxy, formyl and amino.

2. The compound according to claim 1, the pharmaceutically acceptable acid or base addition salts thereof, the stereochemically isomeric forms thereof, or the N-oxide form thereof, wherein:

R$^2$ is Ar$^2$, Ar$^2$-alkyl or Het$^1$;

X is a covalent bond;

Q is O;

R$^1$ is Ar$^1$-alkyl;

Z is a covalent bond or a bivalent radical of formula —CH$_2$— or ≦C(=O);

t is an integer, equal to 0 or 1;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted with an hydroxy radical;

Y is a covalent bond or a bivalent radical of formula —C(=O)— or —SO$_2$—;

L is selected from the group of hydrogen, alkyl, alkenyl, alkyloxy, norbomyl, tricycloundecyl, Ar$^3$, Ar$^3$-oxy, Het$^2$ and mono- and di(Het$^2$carbonyl)amino;

Ar$^1$ is phenyl, optionally substituted with 2 halo-radicals;

Ar$^2$ is naphthalenyl or phenyl, each optionally substituted with 1, 2 or 3 substituents, each independently from each other, selected from the group of halo, cyano, alkyl and alkyloxy;

Ar$^3$ is phenyl, optionally substituted with 1 substituent, selected from the group of alkyloxy, alkylcarbonylamino, methanesulfonyl, alkyl, halo, pyrrolyl and cyano;

Het$^1$ is a monocyclic heterocyclic radical selected from the group of pyrrolyl, furanyl, thienyl, pyridinyl and pyrazinyl; or a bicyclic heterocyclic radical selected from the group of quinolinyl and indolyl; wherein each mono- and bicyclic heterocyclic radical may optionally be substituted on any atom by one or more alkyl radicals;

Het² is a monocyclic heterocyclic radical selected from the group of pyrrolidinyl, dihydro-2H-pyranyl, pyranyl, tetrahydropyridinyl, tetrahydropyrimidinyl, pyrrolyl, imidazolyl, furanyl, thienyl, oxazolidinyl, isoxazolyl, thiadiazolyl, pyridinyl, 1H-pyridinyl, pyrazinyl, pyridazinyl and tetrazolyl; or a bicyclic heterocyclic radical selected from the group of octabicycloheptyl, quinoxalinyl, benzimidazolyl, benzodioxolyl, benzoxadiazolyl, benzofuranyl or dihydroisobenzofuranyl; wherein each mono- and bicyclic heterocyclic radical may optionally be substituted on any atom with one or more radicals selected from the group of halo, alkyl, oxo and alkyloxycarbonyl;

alkyl is a straight or branched saturated hydrocarbon radical having from 1 to 6 carbon atoms or a cyclic saturated hydrocarbon radicals having from 3 to 6 carbon atoms; each hydrocarbon radical optionally substituted on one or more carbon atoms with one or more radicals selected from the group of trihalomethyl, aminocarbonyl, methyl, t-butyl and cyano; and alkenyl is a cyclic unsaturated hydrocarbon radical having from 3 to 6 carbon atoms and having 1 unsaturated bond.

3. The compound according to claim 1, the pharmaceutically acceptable acid or base addition salts thereof, the stereochemically isomeric forms thereof, or the N-oxide form thereof wherein R¹ is Ar¹methyl and attached to the 2-position or R¹ is Ar¹ and attached to the 3-position.

4. The compound according to claim 1, the pharmaceutically acceptable acid or base addition salts thereof, the stereochemically isomeric forms thereof, or the N-oxide form thereof wherein the R²—X—C(=Q)- moiety is 3,5-di-(trifluoromethyl) phenylcarbonyl.

5. The compound according to claim 1, the pharmaceutically acceptable acid or base addition salts thereof, the stereochemically isomeric forms thereof, or the N-oxide form thereof wherein Y is —C(=O)—.

6. The compound according to claim 1, the pharmaceutically acceptable acid or base addition salts thereof, the stereochemically isomeric forms thereof, or the N-oxide form thereof wherein Alk is a covalent bond or —CH₂—.

7. The compound according to claim 1, the pharmaceutically acceptable acid or base addition salts thereof, the stereochemically isomeric forms thereof, or the N-oxide form thereof wherein L is cyclopropyl.

8. A compound of claim 1 selected from the group of compounds with compound number

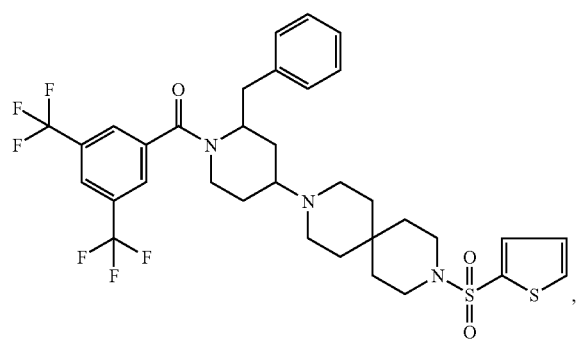

-continued

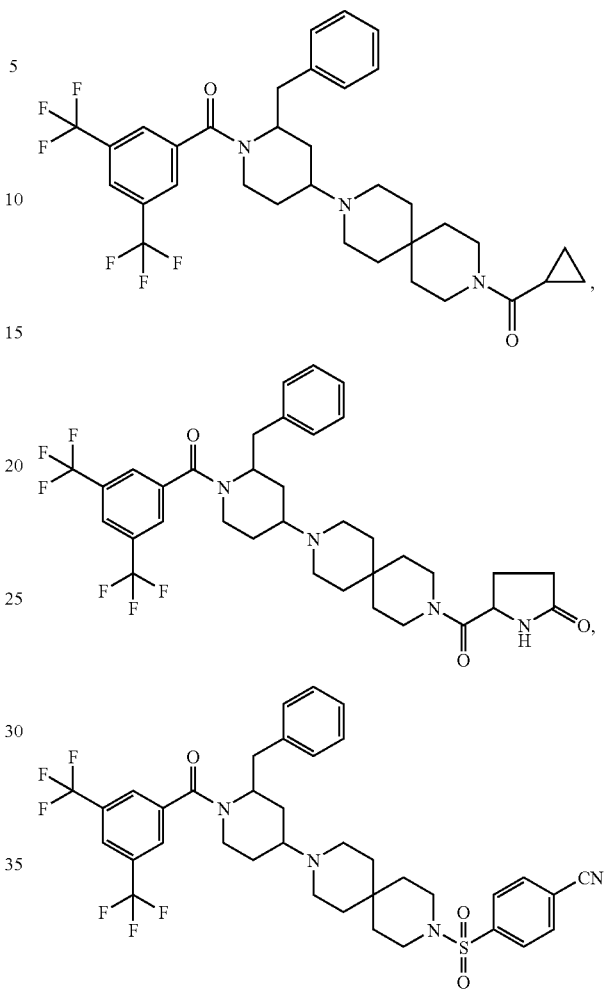

the pharmaceutically acceptable acid or base addition salts thereof, the stereochemically isomeric forms thereof, and the N-oxide form thereof.

9. A pharmaceutical composition comprising a pharmaceutically acceptable carrier and, as active ingredient, a therapeutically effective amount of a compound according to claim 1, the pharmaceutically acceptable acid or base addition salts thereof, the stereochemically isomeric forms thereof, or the N-oxide form thereof.

10. A process for preparing a pharmaceutical composition wherein the pharmaceutically acceptable carrier is intimately mixed with a therapeutically effective amount of a compound as claimed in claims 1, the pharmaceutically acceptable acid or base addition salts thereof, the stereochemically isomeric forms thereof, or the N-oxide form thereof.

11. A process for preparing a compound according to Formula (I) comprising either a) reductively N-alkylating an intermediate compound of Formula (II) with an intermediate compound of Formula (III) to obtain a final compound according to Formula (Ia), wherein all variables are defined as in claim 1, in a reaction-inert solvent and optionally in the presence of an appropriate reducing agent; or

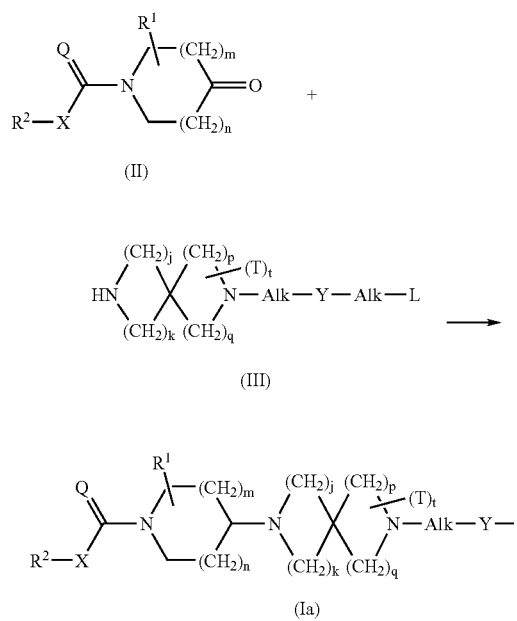

(II)

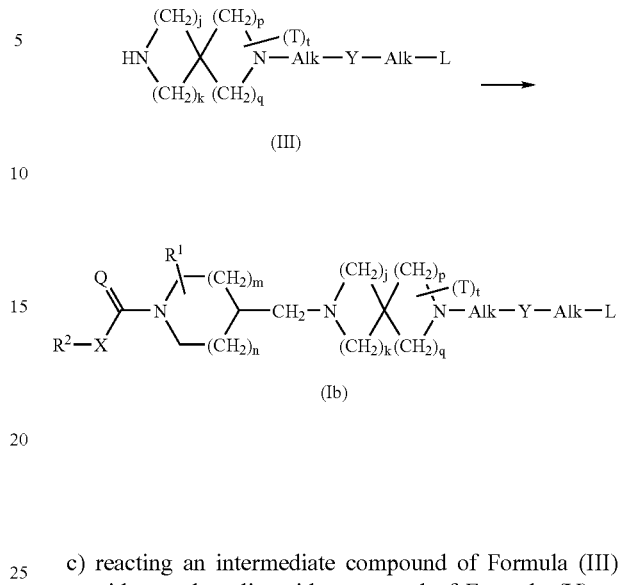

(III)

(Ib)

b) reductively N-alkylating an intermediate compound of Formula (IV) with an intermediate compound of Formula (III) to obtain a final compound according to Formula (Ib), wherein all variables are defined as in claim 1, in a reaction-inert solvent and optionally in the presence of an appropriate reducing agent; or

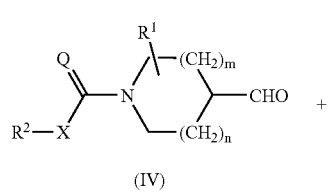

(IV)

c) reacting an intermediate compound of Formula (III) with a carboxylic acid compound of Formula (V) to obtain a final compound according to Formula (Ic), wherein all variables are defined as in claim 1, in a reaction-inert solvent and optionally in the presence of a suitable base; and

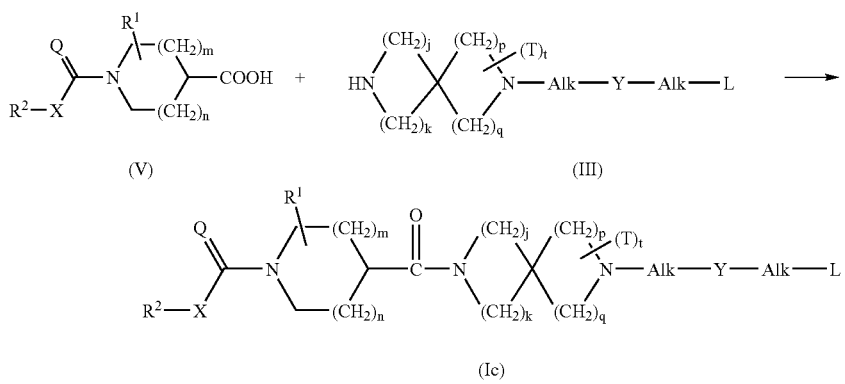

(Ic)

(d) optionally converting compounds of Formula (I), in particular Formula (Ia), (Ib) and (Ic) into each other by transformations, and further, optionally converting the compounds of Formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms, N-oxides thereof and quaternary ammonium salts thereof.

12. The process according to claim 11, wherein the Alk-Y-Alk-L-moiety in the compounds of Formulas (III), (Ia), (Ib) and (Ic) is benzyl.

13. A compound of claim 1 selected from the following

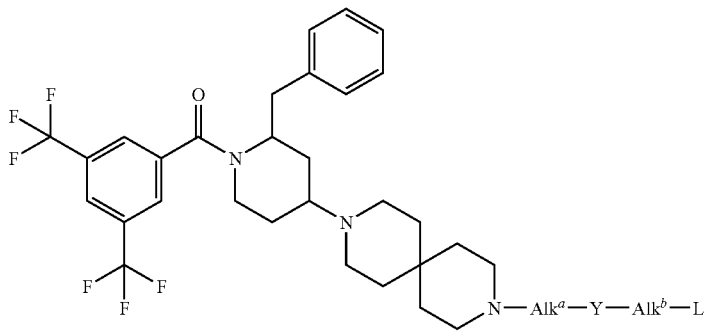

| Comp. No. | Exp. No. | Alk$^a$ | Y | Alk$^b$ | L | stereo descriptors |
|---|---|---|---|---|---|---|
| 93 | B5 | cb | O=S=O | cb | (3-thienyl) | 2R-trans |
| 100 | B5 | cb | O=S=O | cb | (1,2-dimethylimidazol-4-yl) | 2R-trans | and the pharmaceutically acceptable acid or base addition salts, and N-oxide form thereof.

14. A compound of claim 1 that is:

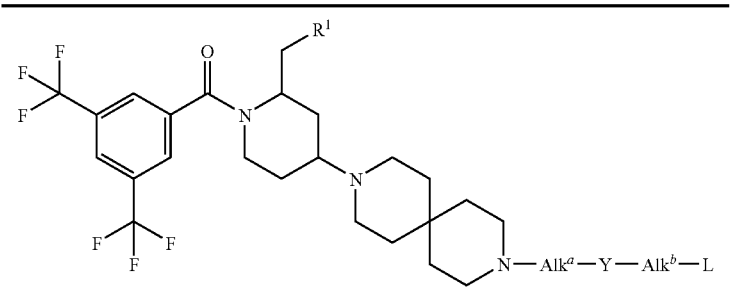

| Comp. No. | Exp. No. | R$^1$ | Alk$^a$ | Y | Alk$^b$ | L | Physical data |
|---|---|---|---|---|---|---|---|
| 132 | B2 | (3,4-dichlorophenyl) | cb | C=O | cb | (tetrahydrofuran-3-yl) | 2R-trans | or a pharmaceutically acceptable acid or base addition salt or N-oxide form thereof.

* * * * *

UNITED STATES PATENT AND TRADEMARK OFFICE
CERTIFICATE OF CORRECTION

PATENT NO. : 7,544,694 B2
APPLICATION NO. : 11/547889
DATED : June 9, 2009
INVENTOR(S) : Frans Eduard Janssens It is certified that error appears in the above-identified patent and that said Letters Patent is hereby corrected as shown below:

Column 15,
Line 12, delete "–CONR$^y$R$^x$," and insert -- –CONR$^y$R$^z$, --.

Column 18,
Line 58, delete "alinetic-rigid" and insert -- akinetic-rigid --.

Column 22,
Line 18, delete "Formula (V)" and insert -- Formula (IV) --.

Column 30,
Line 61, delete "DEPE" and insert -- DIPE --.

Column 35,
Line 66, delete "CH$_2$Cl$_2$/CH$_3$OH/NF$_4$OH" and insert -- CH$_2$Cl$_2$/CH$_3$OH/NH$_4$OH --.

Column 104,
Line 40, delete "–CH$_2$– or $\leq$C(=O);" and insert -- –CH$_2$– or >C(=O); --.
Line 51, delete "norbomyl," and insert -- norbornyl, --.

Column 105,
Lines 53-67, insert compound number -- 92 --.

Column 106,
Lines 1-16, insert compound number -- 3 --.
Lines 17-27, insert compound number -- 4 --.
Lines 28-40, insert compound number -- 119 --.

Signed and Sealed this
Twenty-ninth Day of November, 2011

David J. Kappos
*Director of the United States Patent and Trademark Office*